US012357210B2

(12) United States Patent
Burgoon et al.

(10) Patent No.: US 12,357,210 B2
(45) Date of Patent: Jul. 15, 2025

(54) DISTRIBUTED DISCERNMENT DETECTION SYSTEM WITH PLURAL USER INTERFACE DEVICES

(71) Applicant: DISCERN SCIENCE INTERNATIONAL, INC., Tucson, AZ (US)

(72) Inventors: Judee Burgoon, Tucson, AZ (US); Douglas Derrick, Omaha, NE (US); Aaron Elkins, San Diego, CA (US); John David Mackstaller, Tucson, AZ (US); Jay Nunamaker, Tucson, AZ (US)

(73) Assignee: Discern Science International, Inc., Tucson, AZ (US)

( * ) Notice: Subject to any disclaimer, the term of this patent is extended or adjusted under 35 U.S.C. 154(b) by 710 days.

(21) Appl. No.: 17/662,046

(22) Filed: May 4, 2022

(65) Prior Publication Data

US 2022/0354401 A1    Nov. 10, 2022

Related U.S. Application Data

(60) Provisional application No. 63/184,642, filed on May 5, 2021.

(51) Int. Cl.
*A61B 5/16* (2006.01)
*G06F 3/01* (2006.01)
*G06F 3/041* (2006.01)

(52) U.S. Cl.
CPC ............. *A61B 5/164* (2013.01); *A61B 5/163* (2017.08); *G06F 3/013* (2013.01); *G06F 3/041* (2013.01)

(58) Field of Classification Search
CPC .......... A61B 5/164; A61B 5/163; G06F 3/013
See application file for complete search history.

(56) References Cited

U.S. PATENT DOCUMENTS 9,524,464 B2    12/2016 Davulcu et al.
10,248,804 B2 *  4/2019 Valacich ................ A61B 5/164
(Continued)

FOREIGN PATENT DOCUMENTS

CA         2948390 A1    12/2015

OTHER PUBLICATIONS

Nathan Twyman et al, Autonomous Scientifically Controlled Screening Systems for Detecting Information Purposely Concealed by Individuals, Journal of Management Information Systems, Dec. 2014, Research Gate, Internet.
(Continued)

*Primary Examiner* — Ibrahim Siddo
(74) *Attorney, Agent, or Firm* — McAughan Deaver PLLC

(57) ABSTRACT

A distributed discernment system that includes discernment server including a processer running a diagnostic program and server interface permitting communications to and from the discernment server where the discernment system communicates with two or more human interface devices, where each human interface device includes display capable of presenting a video segment of a virtual human interviewer asking a question to an interviewee and sensors capable of detecting various responses of a human interviewee to each presented question where the discernment server includes a diagnostic that generates interview instructions to be provided to a plurality of human interface devices over the communications network, wherein the instructions provided to a given human interface device are intended to cause the human interface device to present certain questions to a human interviewee interacting with the device and wherein the discernment server is adapted to receive data from each of a plurality of the human interface devices and analyze (Continued)

such data to provide an assessment of the state of the human interviewee interacting with the human interface device.

20 Claims, 5 Drawing Sheets

(56) References Cited

U.S. PATENT DOCUMENTS

| | | | |
|---|---|---|---|
| 10,524,713 | B2 | 1/2020 | Valacich et al. |
| 2013/0266925 | A1* | 10/2013 | Nunamaker, Jr. ........ G09B 7/00 434/362 |
| 2016/0135751 | A1 | 5/2016 | Valacich et al. |
| 2017/0119295 | A1 | 5/2017 | Twyman et al. |
| 2018/0365784 | A1 | 12/2018 | Sartori et al. |
| 2020/0060598 | A1 | 2/2020 | Palti-Wasserman |
| 2020/0163605 | A1 | 5/2020 | Valacich et al. |
| 2020/0327212 | A1 | 10/2020 | Kedem et al. |

OTHER PUBLICATIONS

Judee K Burgoon et al, An Approach for Intent Identification by Building on Deception Detection, 38th Hawaii International Conference on System Sciences—2005, Jan. 2005, Research Gate, Internet.

Lina Zhou et al, A Comparison of Classification Methods of Predicting Deception in Computer Mediated Communication, Jopurnal of Management Information Systems, Mar. 2004, Research Gate, Internet.

Mark Adkins et al, Advances in automated deception detection in text-based computer-mediated communication, Proceedings of the SPIE Defense and Security Symposium, Jan. 2004, Research Gate, Internet.

Lina Zhou et al, An exploratory study into deception detection in text-based computer-mediated communication, Proceedings of hte 36th Hawaii Conference on System Sciences—2003, Feb. 2003, Research Gate, Internet.

Nathan W Twyman, Automated Human Screening for Detecting Concealed Knowledge, The University of Arizona, 2012.

Lina Zhou et al, Automating Linguistics-Based Cues for Detecting Deception in Text-based Asynchronous Computer-Mediated Communication, Group Decision and Negotiation—Jan. 2004, 2004, Research Gate, Internet.

Bruno Verschuere et al, Autonomic and Behavioral Responding to Concealed Information: Differentiating Orienting and Defensive Responses, Psychophysiology—Jun. 2004, Research Gate, Internet.

Judee K Burgoon et al, Detecting Deception through Linguistic Analysis, Intelligence and Security Informatics Symposium, Tucson, Jun. 2003, Research Gate, Internet.

Judee K Burgoon et al, Detecting Concealment of Intent in Transportation Screening: A Proof-of-Concept, IEEE Transactions on Intelligent Transportation Systems, Apr. 2009, Research Gate, Internet.

Douglas C Derrick, Border Security Credibility Assessments via Heterogeneous Sensor Fusion, Intelligent Systems, IEEE, May 2010, Research Gate, Internet.

Douglas C Derrick et al, Detecting Deceptive Chat-Based Communication Using Typing Behavior and Message Cues, ACM Transactions on Management Information Systems, Aug. 2013, Research Gate, Internet.

Aaron C Elkins et al, Vocal Analysis Software for Security Screening: Validity and Deception Detection Potential, Homeland Security Affairs, Jan. 2012, Research Gate, Internet.

Aaron C Elkins et al, Predicting Users' Perceived Trust in Embodied Conversational Agents Using Vocal Dynamics, Article, Jan. 2012, Research Gate, Internet.

Douglas C Derrick et al, Eye Gaze Behavior as a Guilty Knowledge Test: Initial Exploration for Use in Automated, Kiosk-based Screening, Article, Oct. 2011, Research Gate, Internet.

Gabriel Tsechpenakis et al, HMM-Based Deception Recognition From Visual Cues, Article, Jul. 2005, Research Gate, Internet.

Matthew L Jensen et al, Identification of Deceptive Behavioral Cues Extracted from Video, IEEE Explore, Conference Paper, Oct. 2005, Research Gate, Internet.

Thomas O Meservy et al, Deception Detection through Automatic, Unobtrusive Analysis of Nonverbal Behavior, Intellignet Systems, IEEE, IEEE Explore Oct. 2005, Research Gate, Internet.

Jay F Nunamaker, Jr et al, Establishing a Foundation for Automated Human Credibility Screening, Conference Paper, Jun. 2012, Research Gate, Internet.

Jay F Nunamaker, Jr. et al, Embodied Conversational Agent-Based Kiosk for Automated Interviewing,Journal of Management Information Systems, Jul. 2011, Research Gate, Internet.

Steven J Pentland, et al, A Video-Based Screening System for Automated Risk Assessment Using Nuanced Facial Features, Journal of Management Information Systems, Oct. 2017, Research Gate, Internet.

Douglas P Twitchell et al, Using Speech Act Profiling for Deception Detection, Lecture Notes in Computer Science, Jun. 2004, Research Gate, Internet.

* cited by examiner

DISTRIBUTED DISCERNMENT DETECTION SYSTEM WITH PLURAL USER INTERFACE DEVICES

CROSS REFERENCE TO RELATED APPLICATIONS

This application claims benefit of and priority to U.S. Provisional Patent Application Ser. No. 63/184,642, entitled Distributed Discernment System, filed on May 5, 2021, the entire contents of which are incorporated herein by reference for all purposes.

STATEMENT REGARDING FEDERALLY SPONSORED RESEARCH OR DEVELOPMENT

Not applicable.

REFERENCE TO APPENDIX

Not applicable.

BACKGROUND OF THE DISCLOSURE

Field of the Invention

The present disclosure relates to systems for assessing the underlying state of a human.

Description of the Related Art

Accurate knowledge of the underlying state of a human being can be important for a variety of reasons. For example, knowing whether a particular human individual is acting with benign or malicious intent can be critical to the success of an organization of a process. Every organization is at risk of being victimized by individuals acting with malicious intent, such as hidden insiders or individuals seeking to access a location or service for improper purposes. For example, government entities are subject to spying attacks where individuals seeking to improperly obtain government, defense, and military secrets. In addition, governmental and industrial organizations are subject to theft, fraud, embezzlement, sabotage and industrial espionage, where technology, trade secrets and other forms of intellectual property are obtained improperly. Still further, locations and services such as stadiums, sporting events and airline travel are attacked by individuals seeking to inflict damages on the location or service (or individual at or associated with the service) through acts of terror or violence.

A significant challenge with addressing the threat posed by malicious individuals or groups is that they typically purposefully blend in and give no overt hints of their malicious intent. They try hide in plain sight. They are not subject to easy categorization. They could be anyone from a senior officer of a company to a newly hired janitor. Many malicious actors have outstanding reputations, acknowledged for extraordinary performance, and are well-known to organizations they seek to damage. They can be clever and versatile at hiding the nature of their threats so that it is impossible to anticipate and protect against them, or to take countermeasures before appropriate mitigation processes are fully in place.

Another example of situations where an accurate assessment of the underlying state of a human is important, are those that concern the emotional or mental state of an individual. For a variety of reasons—medical, psychological, emotional, etc.—humans can suffer from various physical, mental, and emotional ailments. Detecting the underlying state (or the change in the underlying state) in a particular human can be important for diagnostic and therapeutic purposes. For example, determining the underlying state of an individual subject to manic states, can provide an indication of whether that individual is complying with recommendations for medical treatment and/or whether modification of such treatment is warranted. As another example, determining that an individual is masking significant rage, resentment, or anger issues can help both diagnose unrecognized situations that can be resolved and avoid injury to the individual and others that can arise from such situations.

Despite the importance of being able to accurately assess the underlying state of human beings, prior attempts to do so have been limited both in terms of their likelihood of success and/or the challenges required for their implementation.

For example, human determination of the underlying state of another human being is generally inaccurate across a large number of situations. This generally poor ability of humans to accurately detect the underlying state of other humans is believed to arise from the—facet of evolution that generally favored humans who developed the instinctive belief the that others tended to be more truthful/trustworthy than not. This act of promoting cooperation and tribal success has resulted in a tendency of humans to accept as true the representations of other human beings as to their emotional state.

While it is true that some individual humans have heightened skills with respect to accessing the emotional state of others, their capacity is not typically applicable to a broad range of individuals from different cultural backgrounds or experiences. Thus, an intelligence officer highly capable of detecting deception with respect to Westerners, may not be as successful in assessing the underlying state of an individual raised in Asia, with a different cultural background. Another issue with human-based human state assessment is that it is not easily scalable. Even of one were to locate individual humans with a heightened capacity to assess the underlying state of others, it would be difficult, expensive, and practically impossible to deploy them in all situations. For example, attempting to use human screeners to assess all potential attendees of a significant sporting event (where over 100,000 individuals may attend) would likely be unworkable on a regular basis. A still further deficiency of human-based assessment is that human assessors often have "blind-spots" when it comes to certain individuals, such as their family, long-time co-workers, or those in whom their society places a significant amount of trust.

In an effort to overcome some of the limitations imposed by human-based systems, approaches have been developed to utilize various technologies to assist in the determination of the underlying state of a human being. However, such attempts have been hampered by many of the same challenges posed by human-based approaches.

For example, to date, accuracy has been a significant issue with technology-based approaches and is such a significant issue that one of the most widely-known technological approaches—the Polygraph—is generally deemed so inaccurate as to not be admissible in a court of law. While other approaches—such as an isolated kiosk-based device—have had more success than polygraphs, the general costs and logistical challenges associated with such systems have generally precluded their widespread adoption.

It is an object of the disclosed subject matter to overcome the described and other limitations of the prior art.

BRIEF SUMMARY OF THE INVENTION

A brief non-limiting summary of one of the many possible embodiments of the present invention is a distributed discernment system comprising: a discernment server including a processer running a diagnostic program and server interface permitting bi-directional communications to and from the discernment server; and a plurality of human interface devices, each human interface device including a display capable of presenting a video segment of a virtual human interviewer asking a question to an interviewee interacting with the human interface device, a plurality of sensors capable of detecting various responses of a human interviewee to each presented question, and a system interface permitting bi-directional communications to and from the human interface system, wherein the diagnostic program running on the discernment server is adapted to generate interview instructions to be provided to a plurality of human interface devices over the communications network, wherein the instructions provided to a given human interface device are intended to cause the human interface device to present certain stimuli to a human interviewee interacting with the given human interface device; and each of the plurality of human interface devices is adapted receive interview instructions from the discernment server over the communication network and, in response to such instructions, to present a video segment of a virtual human interviewer asking a question to a human interviewee, where at least the content of the question is determined from the interview instructions; to receive sensor data reflecting the human interviewee's reaction to the question; and communicate at least some of the received sensor data to the discernment server using the communication network; and wherein the discernment server is adapted to receive data from each of a plurality of the human interface devices and analyze such data to provide an assessment of the state of the human interviewee interacting with the human interface device.

BRIEF DESCRIPTION OF THE SEVERAL VIEWS OF THE DRAWINGS

The following figures form part of the present specification and are included to demonstrate further certain aspects of the present invention. The invention may be better understood by reference to one or more of these figures in combination with the detailed description of specific embodiments presented herein.

Figure 1:
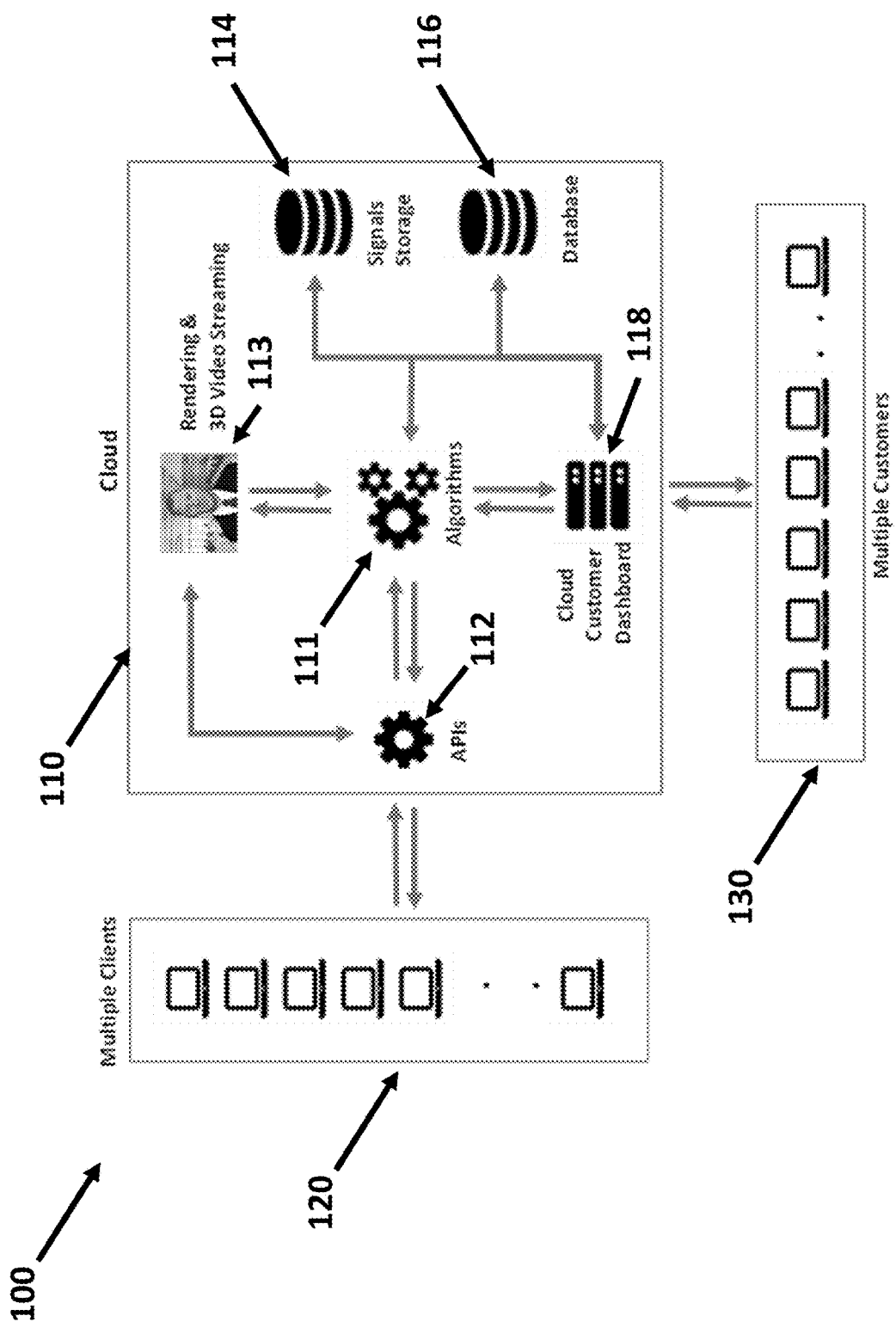
FIG. 1 illustrates an exemplary embodiment of a distributed discernment system constructed in accordance with certain teachings of this disclosure.

While the inventions disclosed herein are susceptible to various modifications and alternative forms, only a few specific embodiments have been shown by way of example in the drawings and are described in detail below. The figures and detailed descriptions of these specific embodiments are not intended to limit the breadth or scope of the inventive concepts or the appended claims in any manner. Rather, the figures and detailed written descriptions are provided to illustrate the inventive concepts to a person of ordinary skill in the art and to enable such person to make and use the inventive concepts.

DETAILED DESCRIPTION

The Figures described above, and the written description of specific structures and functions below, are not presented to limit the scope of what I have invented or the scope of the appended claims. Rather, the Figures and written description are provided to teach any person skilled in the art to make and use the inventions for which patent protection is sought. Those skilled in the art will appreciate that not all features of a commercial embodiment of the inventions are described or shown for the sake of clarity and understanding. Persons of skill in this art will also appreciate that the development of an actual commercial embodiment incorporating aspects of the present inventions will require numerous implementation-specific decisions to achieve the developer's ultimate goal for the commercial embodiment. Such implementation-specific decisions may include, and likely are not limited to, compliance with system-related, business-related, government-related, and other constraints, which may vary by specific implementation, location and from time to time. While a developer's efforts might be complex and time-consuming in an absolute sense, such efforts would be, nevertheless, a routine undertaking for those of skill in this art having benefit of this disclosure. It must be understood that the inventions disclosed and taught herein are susceptible to numerous and various modifications and alternative forms. Lastly, the use of a singular term, such as, but not limited to, "a," is not intended as limiting of the number of items. Also, the use of relational terms, such as, but not limited to, "top," "bottom," "left," "right," "upper," "lower," "down," "up," "side," and the like are used in the written description for clarity in specific reference to the Figures and are not intended to limit the scope of the invention or the appended claims.

Aspects of the inventions disclosed herein may be embodied as an apparatus, system, method, or computer program product. Accordingly, specific embodiments may take the form of an entirely hardware embodiment, an entirely software embodiment or an embodiment combining software and hardware aspects, such as a "circuit," "module" or "system." Furthermore, embodiments of the present inventions may take the form of a computer program product embodied in one or more computer readable storage media having computer readable program code.

Items, components, functions, or structures in this disclosure may be described or labeled as a "module" or "modules." For example, but not limitation, a module may be configured as a hardware circuit comprising custom VLSI circuits or gate arrays, off-the-shelf semiconductors such as logic chips, transistors, or other discrete components. A module also may be implemented as programmable hardware devices such as field programmable gate arrays, programmable array logic, programmable logic devices, or the like. Modules also may be configured as software for execution by various types of processors. A module of executable code may comprise one or more physical or logical blocks of computer instructions that may be organized as an object, procedure, or function. The executables of a module need not be physically located together but may comprise disparate instructions stored in different locations that when joined logically together, comprise the module and achieve the stated purpose or function. A module of executable code may be a single instruction, or many instructions, and may even be distributed over several different code segments, among different programs, and across several memory devices. Similarly, data may be identified and illustrated herein within modules, and may be embodied in any suitable form and organized within any suitable type of data structure. The data may be collected as a single dataset or may be distributed over different locations including over different storage devices, and may exist, at least partially, merely as electronic signals on a system or network. Where a module or portions of a module are implemented in software, the software portions may be stored on one or more computer readable storage media.

When implementing one or more of the inventions disclosed herein, any combination of one or more computer readable storage media may be used. A computer readable storage medium may be, for example, but not limitation, an electronic, magnetic, optical, electromagnetic, infrared, or semiconductor system, apparatus, or device, or any suitable combination of the foregoing. More specific, but non-limiting, examples of the computer readable storage medium may include the following: a portable computer diskette, a hard disk, a random access memory (RAM), a read-only memory (ROM), an erasable programmable read-only memory (EPROM or Flash memory), a portable compact disc read-only memory (CD-ROM), a digital versatile disc (DVD), a Blu-ray disc, an optical storage device, a magnetic tape, a Bernoulli drive, a magnetic disk, a magnetic storage device, a punch card, integrated circuits, other digital processing apparatus memory devices, or any suitable combination of the foregoing, but would not include propagating signals. In the context of this disclosure, a computer readable storage medium may be any tangible medium that can contain or store a program for use by or in connection with an instruction execution system, apparatus, or device.

Computer program code for carrying out operations of one or more of the present inventions may be written in any combination of one or more programming languages, including an object-oriented programming language such as Java, Python, C++ or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. The remote computer may be connected to the user's computer through any type of network, including a local area network (LAN) or a wide area network (WAN), or the connection may be made to an exterior computer for example, through the Internet using an Internet Service Provider.

Reference throughout this disclosure to "one embodiment," "an embodiment," or similar language means that a particular feature, structure, or characteristic described in connection with the embodiment is included in at least one of the many possible embodiments of the present inventions. The terms "including," "comprising," "having," and variations thereof mean "including but not limited to" unless expressly specified otherwise. An enumerated listing of items does not imply that any or all of the items are mutually exclusive and/or mutually inclusive, unless expressly specified otherwise. The terms "a," "an," and "the" also refer to "one or more" unless expressly specified otherwise.

Furthermore, the described features, structures, or characteristics of one embodiment may be combined in any suitable manner in one or more other embodiments. In the following description, numerous specific details are provided, such as examples of programming, software modules, user selections, network transactions, database queries, database structures, hardware modules, hardware circuits, hardware chips, etc., to provide a thorough understanding of embodiments of the disclosure. Those of skill in the art having the benefit of this disclosure will understand that the inventions may be practiced without one or more of the specific details, or with other methods, components, materials, and so forth. In other instances, well-known structures, materials, or operations are not shown or described in detail to avoid obscuring aspects of the disclosure.

Aspects of the present disclosure are described below with reference to schematic flowchart diagrams and/or schematic block diagrams of methods, apparatuses, systems, and computer program products according to embodiments of the disclosure. It will be understood by those of skill in the art that each block of the schematic flowchart diagrams and/or schematic block diagrams, and combinations of blocks in the schematic flowchart diagrams and/or schematic block diagrams, may be implemented by computer program instructions.

Such computer program instructions may be provided to a processor of a general-purpose computer, special purpose computer, or other programmable data processing apparatus to create a machine or device, such that the instructions, which execute via the processor of the computer or other programmable data processing apparatus, structurally configured to implement the functions/acts specified in the schematic flowchart diagrams and/or schematic block diagrams block or blocks. These computer program instructions also may be stored in a computer readable storage medium that can direct a computer, other programmable data processing apparatus, or other devices to function in a particular manner, such that the instructions stored in the computer readable storage medium produce an article of manufacture including instructions which implement the function/act specified in the schematic flowchart diagrams and/or schematic block diagrams block or blocks.

The computer program instructions also may be loaded onto a computer, other programmable data processing apparatus, or other devices to cause a series of operational steps to be performed on the computer, other programmable apparatus or other devices to produce a computer implemented process such that the instructions that execute on the computer or other programmable apparatus provide processes for implementing the functions/acts specified in the flowchart and/or block diagram block or blocks.

The schematic flowchart diagrams and/or schematic block diagrams in the Figures illustrate the architecture, functionality, and/or operation of possible apparatuses, systems, methods, and computer program products according to various embodiments of the present inventions. In this regard, each block in the schematic flowchart diagrams and/or schematic block diagrams may represent a module, segment, or portion of code, which comprises one or more executable instructions for implementing the specified logical function(s).

It also should be noted that, in some possible embodiments, the functions noted in the block may occur out of the order noted in the figures. For example, two blocks shown in succession may, in fact, be executed substantially concurrently, or the blocks may sometimes be executed in the reverse order, depending upon the functionality involved. Other steps and methods may be conceived that are equivalent in function, logic, or effect to one or more blocks, or portions thereof, of the illustrated figures.

Although various arrow types and line types may be employed in the flowchart and/or block diagrams, they do not limit the scope of the corresponding embodiments. Indeed, some arrows or other connectors may be used to indicate only the logical flow of the depicted embodiment. For example, but not limitation, an arrow may indicate a waiting or monitoring period of unspecified duration between enumerated steps of the depicted embodiment. It will also be noted that each block of the block diagrams and/or flowchart diagrams, and combinations of blocks in the block diagrams and/or flowchart diagrams, may be implemented by special purpose hardware-based systems that perform the specified functions or acts, or combinations of special purpose hardware and computer instructions.

The description of elements in each Figure may refer to elements of proceeding Figures. Like numbers refer to like elements in all figures, including alternate embodiments of like elements. In some possible embodiments, the functions/actions/structures noted in the figures may occur out of the order noted in the block diagrams and/or operational illustrations. For example, two operations shown as occurring in succession, in fact, may be executed substantially concurrently or the operations may be executed in the reverse order, depending upon the functionality/acts/structure involved.

FIG. 1 illustrates one exemplary embodiment of a distributed discernment system 100 constructed in accordance with certain teachings of this disclosure. As illustrated in the figure, in this general embodiment, the distributed discernment system comprises three main components: (a) one or more discernment server systems 110 (identified by the box labeled "CLOUD"); (b) a plurality of human interface systems 120 (identified by the computer-like images in the box labeled "MULTIPLE CUSTOMERS"); and (c) one or more communication networks (unlabeled arrows) permitting bi-directional communication between the discernment server system 110 (or systems) 110 and the human interface systems 120 (identified by the gray bi-directional arrows between the human interface systems 120 and the discernment server system(s). In the exemplary embodiment, apparatuses 130 are also provided to allow authorized persons and entities to access the discernment server system 110 for modifying or adjusting the discernment server system 110, receiving reports concerning the operation of the system, receiving analysis and/or reports concerning one or multiple human interactions conducted by the system, or for any other purpose. These apparatuses 130 are generally illustrated by the box labeled "MULTIPLE CUSTOMERS."

In the exemplary embodiment, each of the human interface systems 120 is used to initiate an interaction with a specific human. For purposes of this disclosure, a discrete grouping of interactions between the distributed discernment system and a human individual is referred to as an "interview" and the human individual involved in a given interview is referred to as an "interviewee."

It should be understood that an interview may consist of one or a more different interactions between the discernment system 110 and a given interviewee, and that the interactions may take the form of the provision of various different stimuli to the interviewee and the detection of the response (or responses to those stimuli). For example, in one form, an interview could involve interactions where questions are visually presented to an interviewee and the interviewee is requested to respond by typing answers on a keyboard. In other embodiments, the interview could take the form of an interactive interface that utilizes a virtual person to conduct a verbal question-and-answer interrogation of the interviewee, where questions are posed verbally and the interviewee is requested to articulate their response. In still other examples, the interactions could take the form of the presentations of images, sounds, smells, or the like to the interviewee and the determination of the interviewee's responses to those stimuli. Still further, the interactions comprising an interview could take the form of a combination of the above-described and other forms of stimuli.

In addition to presenting the communications giving rise to the interview to the interviewee, the human interface system 120 will also detect certain reactions of the interviewee to the stimuli. For example, the human interface system 120 can include microphones to capture the interviewee's audible response to presented questions. It can also include a camera and an eye tracker for detecting the interviewee's posture and eye gaze during the interview. It could also include a variety of other detectors and sensors for detecting other responses from the interviewee, such as posture changes, pulse rate changes, changes in skin activity (e.g., pore opening, sweating, temperature changes, etc.). As described in more detail below, the human interface system(s) 120 will transmit data reflecting the sensed and detected attributes of the interviewee to one or more discernment server systems.

In the illustrated embodiment, the discernment server system(s) 110 interacts with the human interface systems 120 (through the communication system(s)) in such a manner that the discernment server system 110 determines a variety of desired interactions for a given interview. These interactions can either be scripted—in the sense that for a certain interviewees or groups of interviewees—the same series of questions can always be presented in the same order or dynamic. In a dynamic interview, for a given interviewee, the discernment server system(s) 110 will request the human interface system 120 to establish certain interactions with the interviewee and will then use the responses received from certain initial interactions to determine which (if any) subsequent interactions to request.

At a high level the operation of this illustrated embodiment is as follows.

At a first time a human interviewee will interact with a specific one of the human interface systems 120 in a manner that causes the involved human interface system 120 to send a notice to one or more of the discernment server systems 110$m$ that it is time to initiate an interview. In response to the signal, one or more of the discernment server system(s) 110 will cause to be communicated to the specific local device 120 requests for one or more interactions and (in some embodiments) requests for certain detected data.

The requested interactions (e.g., a requested series of questions and video displays) will then be presented to the interviewee by the specific human interface system 120 and the interviewee will interact with the human interface system 120 in response to the one or more initial interactions. The response (or responses) received by the human interface system 120 will then be transmitted from the human interface system 120 to the discernment server system 110 (either with or without some local processing). The discernment server system 110 will then receive and process the received response(s) and, in response, may generate a subsequent set of requested interactions to be transmitted to the human interface system 120. The human interface system 120 can then present the subsequent interactions to the interviewee and receive responses from the interviewee. The process may be repeated a number of times with a number of subsequent interactions presented to the interviewee and a number of subsequent responses received by the discernment server system.

In the above example, the discernment server system 110 can then process the received response to provide a general assessment of the underlying state of the interviewee. For example, in applications where the system is utilized to determine the extent to which the interviewee is likely to be engaged in malicious or unauthorized activity with respect to an employer, the discernment server system 110 may generate an indication of the general assessed potential that the individual is (or is likely to engage in) malicious or unauthorized activity (e.g., deception detected, medium risk, low risk, no anomalies detected). As another example, in applications where the system is used for access control at a sporting event, the system may either automatically open a gate to permit an individual to pass through into the event or actuate a mechanism to direct the interviewee to an area dedicated to secondary or more through screening.

By judiciously determining where and how various aspects of the described process are implemented, the embodiments of the present system provide a highly flexible, highly scalable, cost-effective and robust system for discerning the underlying state of humans suitable for a large number of applications.

Various aspects, and several of the many possible alternative embodiments of the exemplary distributed discernment system will be exemplified below. When considering the following written description it will be understood by those of skill in the art that the various embodiments are non-limiting and structural components and/or functional characteristics may be combined, a la carte style, to provide systems having various structural configurations and functionality. For example, and without limitation, as discussed in more detail below, each of the human interface system 120s in a particular embodiment of the distributed discernment system may take the form of any of a stationary system, a mobile system, a desktop system, a tablet-based system, or a smartphone system, and other interface systems that may be envisioned by those of ordinary skill in the art. The discussion of an embodiment utilizing desktops is in no way intended to preclude a system that would combine human interface system 120s having other forms such as a desktop form, a tablet form, and/or smartphone forms. Those ordinarily skilled in the art may practice the inventions taught and disclosed herein with these and many other forms and combinations. Accordingly, unless explicitly noted otherwise, all exemplary embodiments and all exemplary variant embodiments disclosed herein should be understood to be combinable with all other envisioned embodiments and variants to achieve the stated purposes and results of the inventions described herein.

THE HUMAN INTERFACE SYSTEM 120: As generally described above, each human interface system 120 of the present disclosure is a system that permits the overall system to interface with one or more human interviewees to both: (a) present stimuli to a human interviewee and (b) receive and detect attributes of a human interviewee, including specifically responses from a human interviewee to provided stimuli.

Stimuli and Output Apparatus: The stimuli provided to each human interviewee, and the apparatus within each human interface system 120 providing such stimuli, can vary depending on the application of the overall system. In a most basic case, the stimuli can consist solely of audible stimuli in the form of questions presented to the human interviewee. In such embodiments, the human interface system 120 may necessarily include one or more audio speakers for providing the audible messages.

In more typical embodiments the stimuli provided by the human interface system 120 may include audible stimuli (described above) and visual stimuli. As with the audible stimuli, the visual stimuli may take various forms including but not limited to words, static images, video clips, holographic images, displayed 2D or 3D images, displayed physical objects, moving apparatuses, a virtual human agent (which could take the form of a 2D or 3D moving image, a hologram, a robot, an animatronic figure, a cartoon-like humanoid character), or any other suitable form.

Detected Attributes and Sensors: The specific interviewee attributes detected by the human interface system 120 will vary depending on the application, the nature of the stimuli provided for a specific embodiment, and other factors, such as cost, size and bandwidth constraints that may be placed on the system. In many preferred embodiments, the detected attributes (and their associated detecting sensors) will be attributes that can be detected non-invasively (i.e., without making physical contact with the human interviewee). Such attributes include, for example, verbal responses, eye movement, general body posture, facial expressions, etc.) In other embodiments, the detected attributes may include (in addition to the non-invasively detectable attribute discussed above) attributes in which some physical contact with the interviewee is required. Such attributes may include, for example, weight/weight-distribution attributes, which require the human interviewee to stand on a force platform or other similar device, and blood-pressure, which may require the interviewee to interact with a pressure cuff. Certain detectable attributes, such as respiration rate, heart rate, and others, can—depending on the nature of the detectors and the processing nature of the system—be detected either non-invasively (i.e., no physical contact with the human interviewee) or invasively.

In a basic case, the human interface system 120 may include detectors for detecting audible/verbal responses from an interviewee, visual information concerning visible aspects of the interviewee and eye movement.

To detect audible/verbal responses a microphone (or microphone array) may be utilized. The received audible data can be analyzed to determine vocalic aspects of the interviewee's responses, such as pitch, pitch-changes, rate of speech, tempo, volume/intensity etc. The received audible data can also be processed to provide linguistic data related to the interviewee's response such as the specific informational content of the verbal response (i.e., what is being said such as "yes", "uh-hu", "I don't know", to much more complicated responses); the extent of pronoun usages as opposed to more specific references such as hedging, avoidance, etc.

To detect visual aspects of the interviewee, one or more cameras may be employed. To detect eye movement, one or more eyer trackers may be utilized. The eye trackers used in the disclosed system may take one of many forms. In certain examples, the eye trackers may be dedicated apparatus built into a specific device. Such dedicated eye trackers may include, for examples, eye trackers available from Tobii, Gazepoint, ISCAN or others. In alternate embodiments, the eye trackers may take the form of wearable devices, such as an interactive "glasses" like device or other eyewear.

In more sophisticated and complex embodiments of systems constructed in accordance with the teachings of this disclosure, detectors may be used to detect a large variety of attributes of the human interviewee. A non-exhaustive list of such attributes, along with a brief discussion of exemplary apparatus that may be used to detect such activity are discussed below.

Kenesic Attributes, such body posture, body movement/shifts, limb (e.g., hand or finger) movement, overall posture, etc. Such kenesic attributes can be determined by analyzing video data, receiving force platform data, or both, or a combination.

Eye-Related Attributes (sometimes referred to as ocular-metrics), such as gaze location (i.e., what spot is the human interviewee focusing on); gaze duration (how long is the human interviewee looking at a specific location); pupil dilation; gaze pattern (is the human interviewee scanning visual stimuli in a raster pattern or is their gaze jumping back and forth to and from a single displayed image); and blinking patterns. Such eye-related attributes can be detected using a dedicated pupil sensor, an eye tracking device that can additionally provide information on gaze location and duration, or—in certain embodiments—through processing of high-quality video imaging of the human interviewee.

Temperature: The temperature of the human interviewee at one or various locations can be detected using thermal sensors. These sensors can be either contact sensors (i.e., sensors that contact the human interview) or non-contact sensors.

Dermal, or skin-related, activity, such as skin pore activation, galvanic skin response, variations in sweat-gland activity, skin conductance etc.: The status of the human interviewee's skin pores (for example, the pores on the fact) with respect to whether they are open, closed, or partially open, can be detected through processing of a high-quality video signal focused on an exposed area of the human interviewee's skin (for example the face and more specifically, the cheeks). Other aspects of the human interviewee's skin condition, such as galvanic skin response, can be detected through the use of invasive sensors (e.g., contact electrodes).

Heart rate/pulse: The human interviewee's heart rate can be detected through the use of an invasive sensor (i.e., one requiring contact with the human interviewee) such as a blood pressure cuff or through non-invasive approaches such as analysis of high-quality video or thermal data associated with the interview.

Blood pressure: Blood pressure will typically be measured through the use of an invasive sensor (such as a blood pressure cuff), although aspects of blood pressure can be inferred from analyzing aspects of a high-quality video of the human interviewee during the interview.

Facial movements, including micro-expressions: Facial movements (including micro-expressions) can be detected by analyzing high quality video of the human interviewee.

Body movement, postural anomalies, body rigidity, posture/stance: These body-related attributes can be detected by analyzing a video feed of the human interviewee during the interview, through the use of an apparatus like a force platform that directly detects movement, and/or through a combination of video analysis and direct sensors. In certain alternative embodiments, such body movement attributes may be detected through the use of a wearable device (e.g., a vest-like device) that includes gyroscopic or other sensors capable of providing data pertinent to determining or inferring body movement attributes of an interviewee.

Brain activity: brain activity can be detected directly through an invasive sensor (such as an EEG) or through non-invasive sensors (which can sense for emitted detectable signals or the interaction of a brain-emitted signal with another signal, such as a high-frequency signal emitted by a sensor and detected by a receiver).

Biometrics sensors: In addition to the sensors described above, the human interface system 120 may also include one of more sensors for interacting with the human interviewee in such a way that a unique identity of the interviewee can potentially be verified. Such sensors may include, for example, fingerprint sensors, iris-pattern detectors or other devices for sensing attributes considered to be unique to a given individual.

Document/token sensors: In addition to the sensors described above, the human interface system 120 may also include one of more sensors for reading and/or detecting attributes of documents or tokens associated with a human interviewee. Such sensors may include, for example, document scanners, passport readers, RFID readers, bar-code scanners, magnetic strip readers, etc.

PHYSICAL FORM OF THE HUMAN INTERFACE SYSTEM 120: The specific form of the human interface system 120 will vary from application to application and need not be consistent within a given implementation of the described overall system. For example, the human interface system 120 may take the form of a generally fixed system that will typically be positioned at one location within a space and will remain at that location for extended periods of time or permanently. The human interface system 120 may also take the form of a mobile system that can be easily moved from location to location as needed for various applications. In yet further examples, the human interface system 120 can take the form of a semi-mobile "home" apparatus that can easily be transported and used in a home location. Further details concerning variant implementations of the human interface system 120 are discussed below:

Generally Fixed Systems: Certain or all of the human interface system 120 may take the form of generally fixed systems. Such systems are characterized as "generally fixed" because they are not easily movable. A generally fixed system is not necessarily a system that is affixed to a particular location. As an example, a single large kiosk structure may be described as a "generally fixed" system because it is not easily and quickly movable by a single individual, even though the kiosk may be removable within a given location or space.

Because a generally fixed system will typically be intended for long-term use at a single location for a substantial period of time, such systems may utilize more bulky, expensive, and complex systems that other systems. For example, instead of using a small monitor screen for the display of visual images and videos to a human interview, such a system may use a more complicated display such as a large projection screen, a shaped screen in a humanoid form placed in a three dimensional environment (to provide a more realistic presentation of a virtual interviewer), a hologram, or, in some instances, a animatronic robot, designed to mimic all or part of the body of an actual human. In embodiments where a robot will be used with individuals having special interactive needs (e.g., small children or individuals with various processing difficulties)—such as in a hospital or therapeutic environment—the robot may take the form of an animal-like or cartoon-like character to produce an environment more conducive for that particular type of interview.

Dedicated Distributed Generally Fixed Systems: In certain embodiments, the human interface system 120 may take the form of a dedicated distributed system that includes discrete apparatuses and sensors designed to provide a high-fidelity interview environment and where the responses from the interviewee can be detected with significant precision. Such embodiments may involve the utilization of a dedicated room that includes a number of output apparatus and sensors including some or all of the following: a force platform, multiple speakers arranged for dimensional sound control, multiple high-definition screens to provide visual outputs to the interviewee, actuators to provide kinesthetic or haptic output to the interview (e.g., vibrations, etc.). Since such embodiments may typically involve a specific location and numerous sensors, invasive interface devices such as blood pressure monitors, eye tracking goggles, vests with sensors to detect movement, and the like may be used. By providing such a broad range of output apparatus and detectors, a distributed generally fixed system may provide a virtual reality type experience for the interviewee in which as many variables of the interviewee's sensory experience are controlled and dictated by the user interface system as possible.

Generally Fixed Desktop System: A further version of a generally fixed user interface system may be a desktop-based system. Such a system may include, for example, a dedicated computer that includes a video monitor for providing visual stimuli for use in interviews, such as video of a virtual interview agent. Such a system may also include integrated or separate speakers for audio output and HD camera and a microphone for detecting interviewee responses. In general, such a system may also include an eye tracking device. Generally fixed desktop systems are of potential benefit for applications where a number of users can easily be directed to the same location for an interview such as, for example, in applications where the device will be used for employment pre-screening and regular post-employment screening of employees.

Mobile Systems: As described herein, a mobile human interface system 120 is a system that is designed to be relatively easy to move when compared to generally fixed systems. Mobile systems can be beneficial in applications where a system may need to be periodically moved, such as in an airport, where security screening stations may need to be moved on an annual (or more frequent) basis to accommodate new equipment or access applications—such as event access at a given local—where the scale of the system may need to be adjusted to address changes in the anticipated number of event attendees. Mobile systems may also be beneficial in applications where the human interface system 120 may need to be regularly moved during operation to either bring the human interface system 120 to a specific user who has disabilities precluding use of a more-fixed system or to a user who is apprehended and stopped in a specific location (e.g., a trespasser caught by a robotically movable human interface system 120 in an unexpected location of a warehouse). As described in more detail below, mobile human interface system 120s may also be of beneficial use in applications where it is desirable to catch a human interviewee "off-guard" by conducting an interview at a generally unexpected location and time. For example, in an airport security environment, most potential passengers expect to be screened at a dedicated screening checkpoint. Through the use of a mobile human interview, a screening interview can be conducted either prior to the main screening location (e.g., by taking a potential passenger out of the screening line aside for an interview) or long after a potential passenger has cleared the initial screening (e.g., at the gate, just prior to boarding).

Figure 2:
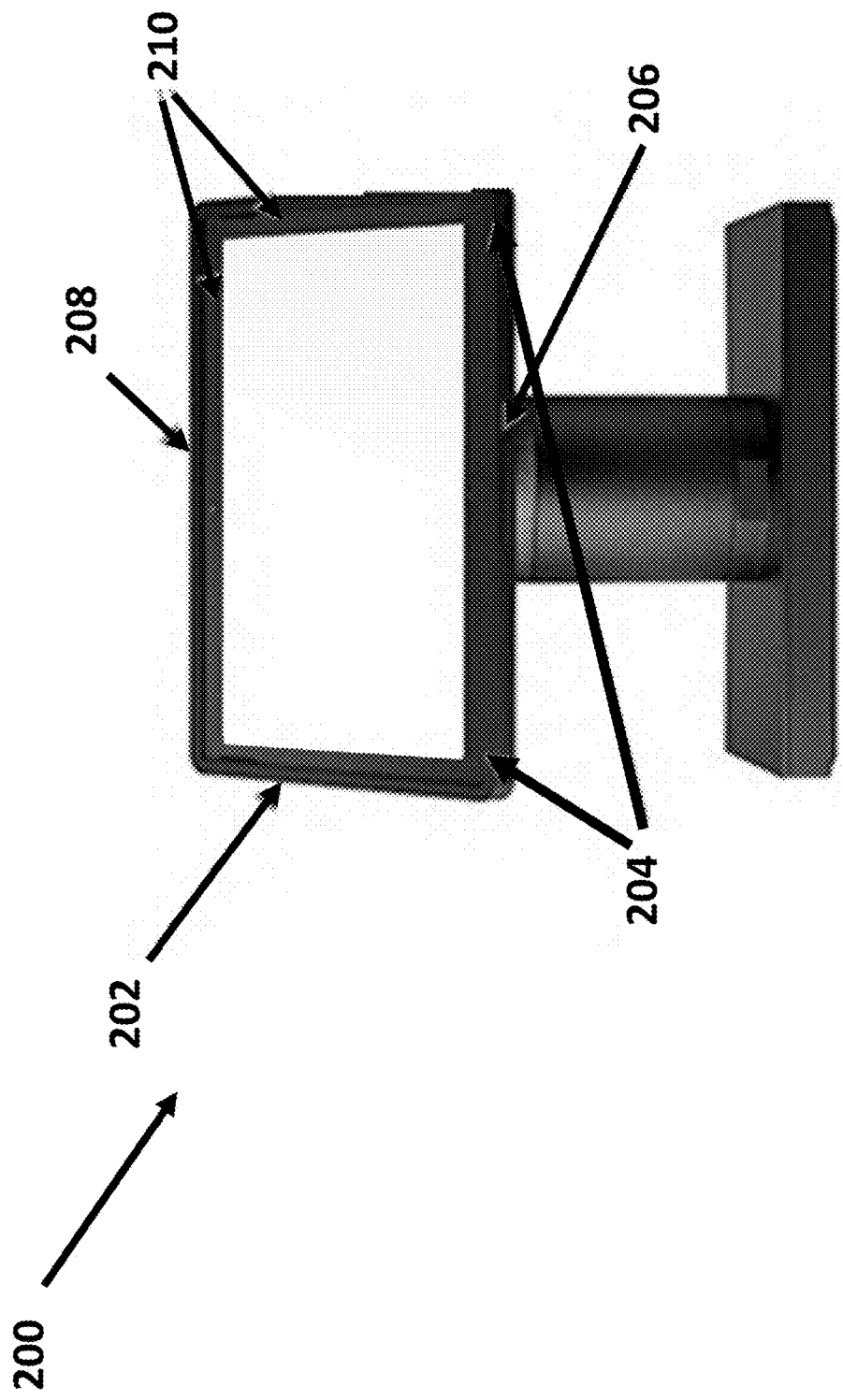
FIG. 2 illustrates an exemplary embodiment of a human interface system 120 taking the form of a generally mobile integrated local appliance.

Additional details of mobile forms that the human interface system 120 may take are discussed below:

Generally Mobile Integrated Appliance:

In one embodiment, the human interface system 120 may take the form of a generally mobile integrated appliance 200 where the generally mobile integrated appliance 200 may have a form factor somewhat like a tablet computer. FIG. 2 illustrates an exemplary embodiment of a human interface system 120 taking the form of a generally mobile integrated local appliance 200.

As depicted in FIG. 2, the local appliance 200 may take the form of a robust and rugged tablet computer. The local appliance 200 may be of such a size that it is suitable for handheld use and/or for use as a table/desk-mounted or resting device and/or as a device that may be mounted on an articulated arm for variable positioning. When used with a variable arm, the local appliance 200 may either be affixed to the arm or coupled to the arm in such a way that it can easily be de-coupled and moved. In further embodiments, the local appliance 200 may be connected through the arm or an alternate mounting structure to a power supply to eliminate direct dependency on a battery. In many embodiments, the local appliance 200 may be tethered to a non-moving or difficult-to-move structure to reduce the potential that the local appliance 200 will be lost, misplaced, or stolen.

In general, the local appliance 200 will include a processor, which may take the form of a system on a chip ("SOC") or system on a module ("SOM") processor and, optionally, one or more application processors, graphical processing units ("GPUs") and/or hardware accelerators. In embodiments where a SOM device is used, the SOM may take the form of a Qualcomm Snapdragon QCS8250 or similar processor.

In embodiments including a SOM, the SOM may provide the computing, memory, storage, wireless connectivity, and the basic I/O functionality for the local appliance. The SOM may also include built-in WiFi/BT circuitry, a MIPI to HDMI bridge, an audio codec & amplifier to interface with a microphone array and speakers & battery management. The SOM may also include I/O ports such as Camera MIPI CSI ports, Display MIPI DSI port, HDMI signals, High Speed PCIe x2, USB3.x, and low speed interfaces like I2C, UARTs & GPIOs that may be terminated on a plug in an edge connector. The SOM may follow the industry standard SMARC form factor. However, the edge connector pin function may be extended to accommodate additional interfaces beyond those defined by the SMARC standard.

The local appliance 200 may also include memory in the form of systems memory and local onboard storage. Embodiments are envisioned wherein the local appliance 200 takes the form of a relatively small, low-cost device, with minimal memory and storage. For example, embodiments are envisioned wherein the system memory is between about 7-10 Gigabytes and the onboard storage is between about 120-140 Gigabytes.

The local appliance 200 may typically also be provided with equipment capable of supporting bi-directional communications with other devices. The is specific type of communications enabled by such hardware may vary from implementation to implementation and may, for example, take the form of hardware enabling WLAN, WWAN, WiFi (Dual Band), WiFi 6, Cellular (including 5G), Bluetooth, Ethernet, USB, or similar media.

The local appliance 200 may also include a display 202, which may take the form of a LED panel with capacitive touch functionality.

The local appliance 200 may also be configured to interact with a number of sensors and detectors to permit the local appliance 200 to detect various attributes and characteristics of an interviewee undergoing an interview. Such sensors and/or detectors may be integrated into the local appliance, or arranged to communicate with the local appliance, using one or more of the communication approaches discussed above. Such sensors and detectors may include, for example, all or a subset of the following components discussed below.

For example, the local appliance 200 may include a High-Definition face streaming camera 208 for detecting the facial movements of the interviewee. While such a camera will typically be integrated into the local appliance, such a camera may take the form of a separate component that provides a data feed to the local appliance 200 via wired or wireless communications. Still further the local appliance 200 may interact with a plurality of facial streaming cameras, with all or some of the plurality of cameras being integrated into the local appliance. The use of a plurality of face streaming cameras can permit the local appliance 200 to receive data feeds that are either duplicative (for error detection and/or correction) or different. Note that still further embodiments are envisioned where streaming cameras are used to not only detect the facial attributes of the interview but also other attributes of the interviewee during the interview, such as respiration rate (e.g., breaths per minute), overall movements (e.g., still or fidgety), or other visibly observable attributes. In one embodiment, the face camera 208 is mounted on an upper bezel of the device 200.

As another example, the local appliance 200 may also include an eye tracker 206. While embodiments are envisioned wherein the same camera used as a face streaming camera provides data for use in connection with eye tracking, for many embodiments, use of a dedicated eye tracker component (which may include one or more cameras and a processor for processing data from such a camera) may be preferred. For example, embodiments are envisioned wherein the eye tracker may be one of the types offered by Tobii that provides real-time data streams corresponding to gaze point, eye position, pupil diameter, user presence, and head pose.

To capture audio inputs, the local appliance 200 may include an integrated microphone 210 and/or be capable of receiving signals form one or more separate external microphones. Such microphones may be general in nature or highly directional. For example, to detect subtle changes in the respiration of the interview, directional microphones targeting the area around the interviewee's nose and mouth may be used. In the exemplary embodiment of FIG. 2, the local appliance 200 may include a microphone array 210 positioned along both the horizontal and the vertical bezels of the device 200 to enable accurate audio capture and provide echo and noise cancellation functionality.

To permit audible interaction with the user, the local appliance 200 may also typically include (or be capable of communicating with) an audio speaker 204 or similar device. In the exemplary embodiment of FIG. 2 the is a speaker system that includes both left and right speakers 204.

A variety of other sensors and/or detectors may be included within the local appliance 200 and/or provided to interact with the local appliance. As one example, the local appliance 200 could include (or be adapted to communicate with) a thermal camera to detect temperature changes with an observed region, such as the front face of an interviewee. The local appliance 200 could also include (or be configured to communicate with) one or more biometric sensors capable of providing biometric information about the interviewee, such as a fingerprint scanner or an iris scanner. Still further one or more physiological sensors could be provided to provide information concerning detectable attributes of the interviewee such as general body temperature, heart rate, pulse, respiration rate, or sweat level. Such added physiological sensors may be external to the local appliance 200 and may interface with the external appliance 200 through the use of wired or wireless technology, such as USB or Bluetooth. Embodiments are envisioned wherein the physiological and other sensors (e.g., a gyroscopic sensor to detect movement) are integrated into a wearable device, such as a vest or jacket, that the interviewee can wear during an interview.

Furthermore, the local appliance 200 may be adapted to communicate with a scale or force platform to detect the physical presence of an object (e.g., an interviewee) at a specific location and/or the forces created by an interview across a general area (e.g., is the user shifting weight from one foot to another, pacing, etc.).

In many applications, the local appliance 200 may take the form of a portable device that is not physically linked to any other hardware. In such applications, the local appliance 200 may take a form similar to a tablet device that may be available for the interviewee (or one assisting the interviewee) to handle the device. For other applications, the local appliance 200 may take the form of a device that may be fixed in place and relatively unmovable. In either case, the local appliance 200 may typically operate in conjunction with a power supply that may include a rechargeable battery (which could be integral with the local appliance) or—typically for fixed applications—an external power converter.

FIG. 2 illustrates different attributes of an exemplary local appliance 200 constructed in accordance with certain teachings of this disclosure. In the referenced figures, the local appliance 200 may take the form of a robust and rugged tablet. As reflected in FIG. 2 the local appliance 200 may take the form of a handheld tablet that can be held by a user and/or positioned on a stand. As further reflected in the referenced figure, the local appliance 200 may optionally take the form of a tablet that is affixed to a support structure such as an articulated arm. In these and other exemplary embodiments, the local appliance 200 may be physically tethered to another structure to both permit constant powering of the device (and thus reduce dependance on any internal batteries) and/or minimize the potential for loss or misplacement of the local appliance.

As still further reflected in FIG. 2, the local appliance 200 may take the form of a tablet that defines a central display area surrounded by horizontal and vertical bezels. In the depicted example, one or more of the sensors discussed above may be positioned within the horizontal and/or vertical bezels. For example, an eye tracker assembly 206 may be positioned generally across the central area of the lower horizontal bezel, a face streaming camera 208 may be positioned within the upper horizontal bezel, left and right speakers 204 may be positioned at the left and right intersections of the vertical bezels and the lower horizontal bezel and a microphone array 210 may be positioned partially within the top horizontal bezel and partially within the upper part of the right vertical bezel.

In terms of physical construction, the local appliance 200 may be formed in a variety of ways. In accordance with one approach the local appliance 200 may be formed from several different sub-components or systems. First, a base carrier board is provided that provides structure for enabling base connections between all integrated sensors and detectors and any external peripheral sensors or detectors. The base carrier board may also provide basic system level functions such as power and communication options.

Second, the exemplary architecture may include a pluggable system of a module that provides the general processing and storage functionality and that may provide the hardware necessary to enable base communications. Such a system on module (SOM) may take the form of a basic system that provides the main computing functionality, memory/storage functionality and basic communication and I/O functionality required by the local appliance. It may include built-in Wi-Fi and/or Bluetooth hardware and may further include microphone and speaker interfaces. A standard connector—such as a plug-in connector—may be used to couple the SOM to the base carrier board.

Third, the exemplary architecture may include a group of base peripherals and sensors that may interface with the base carrier board and provide various input signals useful to the system. Note that in the depicted example of FIG. 2, the base carrier board includes unused slots and/or connectors intended to provide expansion capabilities. Such unused slots and/or connectors may enable rapid addition of new sensors in the future.

Active Mobile Systems: Alternate embodiments of the human interface system 120 are envisioned wherein the human interface system 120 may be designed to be movable during use so as to enable interviews to be conducted at various locations and at unexpected times. For example, one embodiment of such a system could involve the coupling of a local appliance 200 as described above with a transportation and power system such as a walking robot (e.g., an agile mobile robot such as the SPOT robot available from Boston Dynamics) or a movable cart with wheels. Such a system could then be guided to a particular interviewee at any location and an interview could then be conducted at an unexpected time and location. Such a system is believed to be of benefit because experience has shown that "surprise" interviews can often produce the most candid (and therefore the most likely to be truthful) responses.

Note that the human interface system 120 format for an active mobile system need not take the form of a local appliance 200 and that alternate forms may be used. For example, an active mobile human interface system 120 could take the form of a walking bi-pedal humanoid robot that includes the output devices and the sensors necessary to conduct the desired interview.

Home Discernment System: A still further variant of the human interface system 120 is a variant designed to be used in a "home" environment, such as an individual household, a hospital room, or any location where a low-cost discernment system is desired. In general, such a system could be designed to take advantage of hardware already typically found in a residential location such as a TV monitor with speakers, a camera and a microphone, and WiFi or Ethernet connectivity. For example, a Home Discernment Device that may take the form of a deck-of-card sized device that is capable of receiving input from a microphone and camera via a standard media (e.g., USB) and that is capable of providing audio and visual output to a TV monitor via a standard interface (e.g., HDMI). The home Discernment Device may also include an input for power and could include a WiFi chipset for communication with a local WiFi network (and subsequent communication with a Discernment Server System) and/or an Ethernet connection. In many applications eye tracking information may be useful or necessary. To accommodate such applications, the Home Discernment Device may also include another input port (e.g., a second USB port) for connection to an eye tracker. The eyer tracker may be associated with the resident's TV to create a basic human interface system 120.

SmartPhone Systems: Given the increasing complexity of smartphones, alternate versions of the human interface system 120 are envisioned where a smartphone serves as a human interface system 120. In such embodiments, an application may be provided to run on a smartphone that would use the front, or "selfie" camera as a camera and a eye tracker, the phone microphone as a microphone, and the display and speakers of the smartphone as audio/visual output devices.

Virtual/Augmented Reality Systems: Still further embodiments are envisioned wherein the human interface system 120 utilizes available virtual reality or augmented reality systems to interact with a human interviewee. For example, available apparatus like the virtual reality system OCULUS QUEST 2 could provide audio/visual/kinetic outputs to an interviewee and could be combined with sensors to provide the feedback signals required by the discernment server system 110 for proper analysis. In still further embodiments, augmented reality interface devices—such as AMAZON's smart specs, MICROSOFT's Hololens 2 headset, or LENOVO's ThinkReality A3 glasses—may be used as all or part of a human interface device.

Anonymization: In certain applications, for privacy and other reasons, it may be desirable for the discernment system to not retain—or even possess at any time—information or data that can be readily used to unique identify the specific human individual being interviewed. In other words, in certain applications it may be beneficial—to the extent possible—to ensure that the discernment process is effectively anonymous in terms of associating the received data and the resultant discernment analysis with a specific unique individual. Various processes and methods may be built into the human interface system 120s (or the overall distributed discernment system) to promote this goal.

In accordance with one embodiment, a unique identifier may be generated for each interviewee that is not directly usable to determine the identity of the human being interviewed. For example, a discernment system constructed in accordance with the teachings of this disclosure may generate a random code or token that will be used to identify each interviewee. In this embodiment, the system (ether within a given human interface system 120 or in the discernment server system) may—at the inception of an interview—generate a random identifier for that interviewee, provide the random identifier to a user of the system (such that the user could associate the interview with a specific human individual) and then provide a discernment report that provides the analytical output for that specific random identifier. The human user of the system, then, could use the report to make a determination with respect to the human individual (e.g., whether to allow them to pass through security).

The code or token used in the processes described above need not be generated randomly as long as the code or token itself cannot readily be used to identify a specific human individual. As such, the code or token could be simply a sequential number associated with a specific human interface system 120, a string based on non-identity data (e.g., a string identifying a location, a human interface system 120 station and, the specific date and time the interview was initiated).

Still further the code or token used by a discernment system 100 constructed in accordance with the teachings of the present disclosure may be generated externally (through a process where the external system that could retain an association of the token with a specific human individual), such that there is an external system that may associate the code or token with a specific human identity, but where the discernment system 100 does not have data that readily enables such an association. For example, if a discernment system 100 constructed according to teachings of this disclosure is used for airport access control, the airport may have a system that generates—for each user—a airport travel ID that is associated with a particular user or a particular flight reservation. That travel ID could then be provided by the airport (or used by the airport to generate a further code or token) that is then provided to the discernment system 100. In such a situation, the data provided to, and processed by, the discernment system 100 could not be used directly to identify a unique human identity associated with a given interview. The airport system, however, which would have data linking the code or token provided to the discernment system 100 to a given unique individual.

The code or token described herein may take several forms. For example, it could take the form of a paper printout that is scanned or read. It could take the form of a physical token provided to a potential human interviewee. It could further take the form of information reflected in a visual display, such as a QR code on a smartphone display.

One limitation of the approach described above (where anonymous codes or tokens are used to identify each interviewee) is that the data captured and analyzed for purposes of the interview assessment could potentially be analyzed to determine the specific human identity of the interviewee. For example, even if an anonymous code or token is used to identify an interviewee, if a malicious actor were to obtain video associated with the interview or an audio of the interview, they may be able to analyze and/or process the captured audio or video data to determine the human identity of the individual associated with the interview (e.g., through facial or voice recognition processes). To protect against such possibilities, embodiments are envisioned wherein some or all of the individual human interface system 120s within the discernment system 100 may perform a process to anonymize certain sensor data as it is received (or prior to its transmission to the discernment server system).

For example, in one of many envisioned embodiments, a software, hardware, or combination software/hardware process may be used to transform certain individual sensor data as it is received into data that cannot be readily used to reconstruct the originally received signal and/or determine the unique identity of the human associated with the received signal. In accordance with such embodiments a received signal (such as a video or audio signal) may be passed through statistical processing and/or an alternative process (e.g., an obfuscation process) to generate a signal that contains or identifies the informational content necessary for the desired discernment analysis (e.g., content that enables determination of the overall body posture of the interviewee but that does not enable the use of facial recognition software).

In alternate embodiments, signals received at the human interface system 120 by sensors may not be modified directly, but rather may be aggregated with other received signals to form an aggregated data package that may then be processed in such a way (e.g., through statistical manipulation or passage through a one-way process) to generate a data package that may be adequately used for discernment analysis but cannot be readily used to identify the specific human individual that resulted in the generation of the data.

In certain embodiments, only some of the signals received by the human interface system 120 may be anonymized. Signals not readily associated with a particular human identity, such as weight, temperature, heart rate, need not necessarily be anonymized. Signals more readily associated with a specific individual, such as the audio or visual signals, however, may be processed to generate anonymous data using one or more of the processes described herein.

As a still further embodiment, applications may be envisioned wherein it may be desirable to anonymize data as described herein throughout the system, but still retain the ability—in very limited instances and subject to very tight user access controls—to associate signals associated with a given interview with a specific human interviewee. In such instances one or more limited access hardware (or software or biometric or a combination) keys or tokens may be generated that are capable of reversing the anonymization process and recapturing either the original interview data and/or other data that would allow an authorized user to associate a given interview with a unique human identity. In such embodiments, the ability to anonymize data generally would be limited by the security measures associated with the described keys or tokens. Such systems may be operated with mandatory access controls (MACs) and/or discretionary access controls (DACs) such as are used in trusted computing environments.

THE COMMUNICATION LINKS: The communication links between the human interface system 120s and the discernment server system 110 may take any suitable form, such as wired connections or wireless connections. In certain embodiments involving mobile devices, the communication channels may include wireless communications with some or all of the human interface system 120s (e.g., through high-speed, high bandwidth 5G connections) coupled with downstream wired connections or further wireless connections.

Encryption: As a security measure, all or part of the data used in a discernment system constructed in accordance with teachings of this disclosure may be encrypted both as it is communicated across any communication link and as processed within the system. Thus, for example, the data received by the human interface system 120 may be encrypted, the data transmitted from the human interface system 120 to the discernment server system 110 may be encrypted, and all reports and/or analysis generated by the discernment server system 110 may be encrypted. Note that any such encryption could be distinct from—or integrated with—the anonymous processes discussed previously.

Thus, for example, one could encrypt data that has not be anonymized (such as a non-anonymized video file). While such a file would be encrypted—in the sense that it would not be readily accessed by those not authorized to receive and view such data—it would not be anatomized because anyone able to decrypt the data file could then use it to identify the unique human associated with the file.

In other embodiments one could both anonymize and encrypt data used by the discernment system either through separate processing steps or through an integrated process where input non-anonymous data is both anonymized and encrypted through a single process step.

As is known to those sufficiently skilled in the art, in addition to using encryption to protect the data from observation, encryption may be used to authenticate the data. That is to say that a device holding a private encryption key may encrypt that data such that it may be verified as being encrypted by that device at a later time.

THE DISCERNMENT SERVER SYSTEM: In one exemplary embodiment the discernment server system 110 (or systems) will take the form of a server or multiple servers that communicate with the human interface system 120s to at least: (a) provide most or all of the information necessary to provide stimuli to the interviewee for an interview; (b) receive detected interview data from the human interview systems; (c) process received detected data in light of the provided stimuli to generate further stimuli interactions with an interviewee and/or to assess and analyze the received signals and to provide a report or indication reflecting the underlying state of the human interview; and/or (d) provide an interface into the discernment server system 110 that may be used to modify the system, adjust the nature of one or more interviews, directly communicate with a human interface system 120, monitor an interview in real time, or request to generate various reports. Other functionality may be enabled by or within the discernment server system.

The precise process by which the discernment server system 110 assesses the underlying state of a human interviewee may vary significantly. For example, in applications where the system is deployed to detect deception at an airport access point, the discernment server system 110 may include one or more machine learning models—created through the use of significant test data—that correlate certain received signals from the human interface system 120 with deception. For example, in applications where an interviewee is asked whether they are transporting certain contraband, and a question is posed with a visual depiction of the contraband, the vocal inflection of the interviewee along with an assessment of the interviewee's eye gaze pattern (e.g., are the focusing on or avoiding focusing on the displayed contraband in an unusual manner) can provide an indication about whether the interview is being truthful in their response. Various approaches for detecting the state of a human interviewee using received sensor data are discussed and disclosed, for example, in U.S. Patent Application Publication No. 2013/0266925.

The physical implementation of the discernment server system 110 may take many forms. In one embodiment the discernment server system 110 may be a computer server (or group of servers) dedicated solely to the distributed discernment system. In other embodiments the discernment server system 110 may be implemented virtually in the cloud such that it is not temporally linked to any specific physical hardware. Hybrid approaches are also envisioned.

As reflected in FIG. 1, in the illustrated example, the discernment server system 110 is a cloud-based system that can be implemented through a local or a distributed computing system. In the illustrated example, the cloud-based system includes one or more application programming interfaces (APIs) 112 that support communications between the discernment server system 110 and the human interface devices 120. The APIs 112 may gather and process the data and information received by one or more of the human interface devices 120 such that it can be processed by one or more discernment detection algorithms 110. The algorithms may utilize data stored in a database 116 for completing the analysis of the provided signals and/or may store reports and—if the embodiment is one where certain signal are stored—signals in a storage device 114.

In the illustrated embodiment of FIG. 1, the algorithms 111 may also provide data that can be used to generate video streaming data to be provided to the human interface devices 120 (through the APIs 112) for conducting all or parts of an interview.

In the example, a cloud customer dashboard 118 may be provided to permit customers with appropriate credentials to utilize one or more of the customer devices 130 to access one or more of the reports stored within the storage system 114 and/or the database 116

SPECIFIC EXEMPLARY EMBODIMENT: A distributed discernment system as described herein may be implemented in such a manner as to provide several advantages not available from localized systems. For example, such advantages include the ability to retain security with respect to certain discernment processes and to advance and develop such processes through the use of data obtained from a large variety of sources and locations. Such an approach also enables the most efficient use of hardware and software such that various processing steps can be handled at the most appropriate location within the system.

In such an exemplary embodiment it may be desirable to have all or substantially all analysis of the detection signals received during a human interview processed within the discernment system 100 such that there is no need to store or retain any of the analytical software or models within the various human interface system 120s. This may be beneficial because wide access to the analytical software or models could allow a malicious actor to learn details of the system that would allow them to increase the chances that they could develop countermeasures to the system. By utilizing a generally centralized discernment server system 110, the most sensitive software and systems may be located (physically and/or virtually) in one or more limited locations where appropriate security measures may be maintained.

In the example described above, the various apparatus required to form the human interface system 120s may be limited to systems that have relatively little "intelligence" in the sense that the human intelligence systems are primarily vehicles to: (a) receive commands from the discernment server system 110 to provide certain stimuli to the human interviewee and (b) return signals received from the various detectors and sensors associated with the human interface system 120 that are received during an interview. In such an embodiment, the various human interface devices would not store any received data from the discernment server systems, from the detectors and sensors that comprise the human interface unit, or have any processing capability to self-generate questions, images, sounds or other stimuli to be provided to the interviewee or to perform any discernment analysis of the signals and detections received by the human interface system 120 during the interview. The human interface system 120, in such an example, would primarily be a non-intelligent conduit through which the discernment server system 110 would communicate with the human interviewees. In the example under discussion, all of the "intelligence" within the system—specifically the generation of the specific questions and other stimuli to be presented to a human interviewee, the determination of the particular form that a virtual depicted interviewer may take (in terms of appearance, voice, dress, mannerisms, etc.) would all be determined and controlled by the discernment server system. So too would all of the processing and analysis of the detected and sensed signals received during an interview and the reporting of the results of such processing and analysis.

Figure 3:
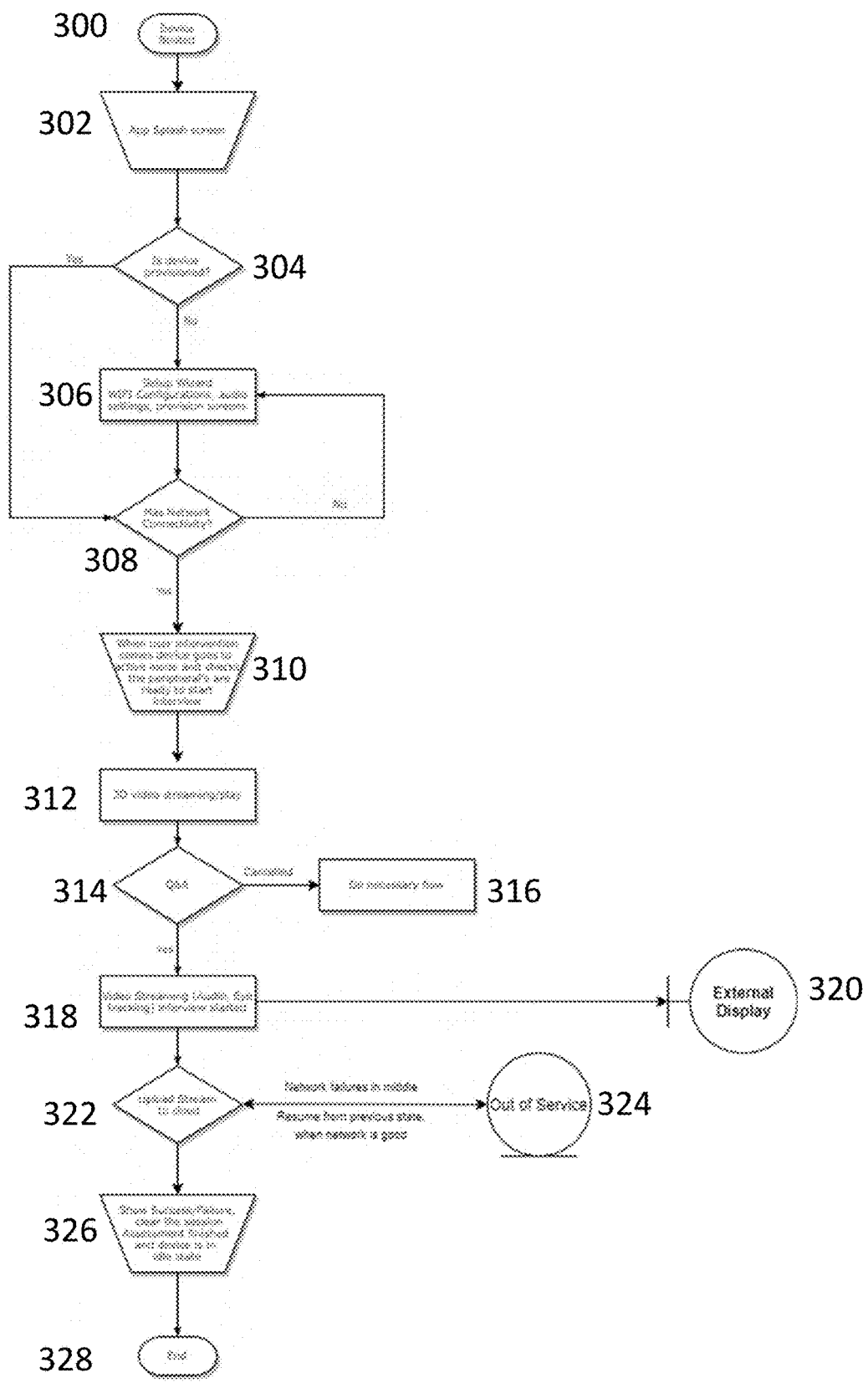
FIG. 3 illustrates the high-level general operating process of an exemplary distributed discernment system with respect to a given human interface unit.

In the exemplary example discussed above, where the various human interface system 120s take the form of thin clients, the overall operating process for an exemplary human interface system 120 could follow the process illustrated by FIG. 3, below. FIG. 3 illustrates the high-level general operating process of an exemplary distributed discernment system with respect to a given human interface unit.

Referring to FIG. 3, the exemplary process begins at a step 300 where the human interface system 120 boots up, typically through a powering on of the apparatus after a state where it is off and non-operable. After the initial boot operation, the human interface system 120 (which in the present example will be discussed in the context of an integrated, generally mobile tablet device) may display a splash screen at a step 302 in which a user or operator of the system may then enable the device through a provisioning step 305 where, if the device was previously provisioned, the specific device may step to a step 308 where it is coupled to one or more communication networks, associated with one or more peripheral devices (e.g., a force platform, printer, etc.)

If the device was not previously provisioned, the system may proceed to a provisioning step 306 where the system— alone or with human intervention—utilizes a plurality of provisioning screens to steps through a set-up wizard that properly establishes any needed WIFI Configurations and audio settings. Once the provisioning step is completed, the device can proceed to step 308 where it is coupled to a communications network.

The human interface may then seek to make communication contact with the discernment server system 110 and, once suitable contact and communications have been made, transition to a step 310 where the device goes to active mode and confirms that its sensors and any peripherals where it is ready to begin a human interview.

Once placed in a "ready to start interview" state the human interface system 120 may need to determine when to start the interview.

In one of many simple approaches, the interview session may be initiated by the interviewee interacting with the local appliance 200 by, for example, activating a touch-screen button. In such an exemplary system, the individual to be interviewed may then be instructed to move to a position where they are within the appropriate detectable area of the sensors and detectors (e.g., guided to move to a spot where their face is properly framed within a video camera) and the interview may then be conducted through the provision of stimuli to the interviewee and the receipt and transmission of detector and sensor values.

The interview may begin with a step 312 where question and answer audio and video data (either streamed to the device 120 or rendered locally) is presented to the interview. The interviewee may then respond to any presented questions and a video stream of the detected signals, e.g., the video, audio, and eye tracking signals) can be obtained.

In the example of FIG. 3, an opinion is provided for canceling the interview and transitioning the system to a canceled state 316.

In the example of FIG. 3, a further option is provided for providing the streamed recorded signals (e.g., video, audio, and eye tracking) externally system that they can be displayed on an external display at step 320. Such external display permits observation of some or all of the conducted interviews.

In the example of FIG. 3, once the interview is completed the stream of obtained signals is uploaded to the cloud-based discernment server system at step 322. If this upload fails, the device 120 will transition to an out of service mode at step 324.

If the upload is successful, the system will transition to a step 326 where the success/failure of the interview and/or the assessment of the interview (e.g., in terms of the likelihood of deception) is reported. The device 130 can then be placed in an idle state or transition to an end state 328.

Once the interview is completed, the interview data may be "wiped" form the human interface system 120, such that no localized record of the interview is maintained, and a report or analysis of the interview may be provided by the discernment server system 110 to authorized users of the system. The report or analysis may be provided in near-real time via electronic devices, or via delayed communications (e.g., emailed or texted reports reflecting the results of a number of different human interviews.

Figure 4:
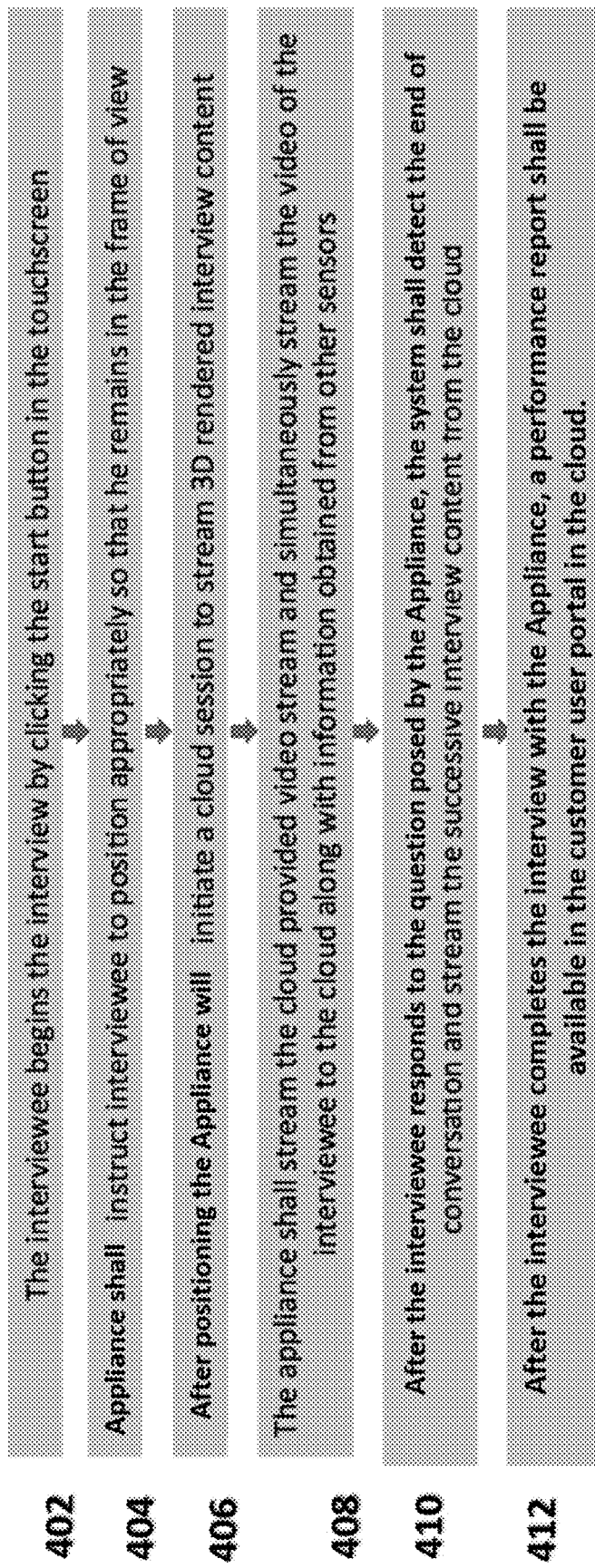
FIG. 4 illustrates an exemplary interview process using a touchscreen start button to start the interview and where the virtual interview agent presented to the interviewee is revered to as the Appliance.

FIG. 4 illustrates an exemplary interview process 400 using a touchscreen start button to start the interview and where the virtual interview agent presented to the interviewee is revered to as the Appliance.

As reflected in FIG. 4, the process begins at step 402 where the interviewee begins by clicking the start button provided on a touchscreen. The system then proceeds to a step 404 where the appliance will instruct the interview such that he or she will remain within the frame of view of the eye tracker and, if provided, face camera used in the interview.

Once proper positioning of the interviewee is confirmed, the system will transition to a step 406 where the local device 120 will initiate a cloud session with the cloud-based server system 110 to stream 3D rendered interview content to the local device 120.

The system will then proceed to a step 408 where the local appliance will stream the cloud-provided video stream to the interviewee and simultaneously stream the video of the interview and information obtained from some or all of the sensors within the local appliance 120 to the cloud-based server system 110.

In step 410, after the interviewee responds to the question posed by the local device, the system will detect the end of the conversant and stream any successive interview content from the cloud to present it to the interviewee.

Finally, in the illustrated example, once the interview completes the interview, the discernment server system 110 will prepare a performance report for the interview that will be made available in the appropriate customer user portal in the cloud. In the illustrated example, this action occurs at step 412.

In some alternate embodiments, a human interface system 120 in the form of a local appliance 200 may be adapted to automatically initiate a session upon the occurrence of one or more events. As an example, embodiments are envisioned where the interview is initiated through the use of an "are eyes found" function within the eye tracker. In such embodiments, the receipt of a signal indicating that the eyer tracker for a particular user appliance 200 has detected the presence of eyes may cause the initiation of an interview with respect to that user appliance.

Still further embodiments are envisioned where the occurrence of a multitude of events is required before the initiation of an interview. For example, embodiments are envisioned wherein the simultaneous detection of a weight above a minimum (through the use of a force platform) and the receipt of a positive "eyes found" signal from the eye tracker may be required for the initiation of an interview.

As may be envisioned by those sufficiently skilled in possession of the teachings and disclosures contained herein, the occurrence of a multitude of events may be required before the initiation of an interview Calibration: As described generally above, the initial parts of an interview may involve a form of calibration where the human interviewee is asked to physically move in such a manner as to better interact with the human interface system 120. Other calibration processes are envisioned. For example, to determine the appropriate operation of eye detecting and eye tracking apparatus a human interviewee may be shown certain images on a display (e.g., dots) and asked to look at and track the dots as they move.

While calibration processes as described herein may be used to physically calibrate the system, certain other interactions with the interviewee may be used to "calibrate" the manner in which the data collected during the interview is processed and analyzed by the detection server system. For example, in certain embodiments the discernment server system 110 may consider the amount of time that passes from the end of a question posed to an interviewee and the start of the interviewee's answering of the question as a data point in assessing the state of the interviewee. While such data may be of significance to an interviewee who is presented questions in (and asked to answer in) their language, such data may not have the same significance for an interviewee questioned in a non-native language. As such, before the substantive portion of an interview is begun, the human interface system 120 may present to the interviewee one or more calibration-type questions (e.g., "Is English your native language?") to help calibrate or tune the analytical or processing operations performed by the discernment server system.

Automatic Advancement of the Interview: One issue that a system, such as the described exemplary embodiment, may have to address is when to advance from one question to another. One of many possible approaches would be to have a "next question" button available to the interviewee or to have the interviewee perform some specific detectible gesture (e.g., tap left foot) to move to the next question. However, the requirement for such actions by the interviewee may potentially disrupt the interview process and make it more difficult for the processes running on the discernment server system 110 to accurately determine the state of the interview. Accordingly, embodiments are envisioned where the distributed discernment system automatically advances the questions presented to the interview.

Automatic advancement may be accomplished by having the system: detect delays in speech or identify certain words of linguistic patterns indicative that the interviewee has completed their answer to a previous question. In another envisioned embodiment, a new question may be asked by the discern server system before the interviewee has completed answering the current question. This process may be used to disrupt the pace of questions and answers in an attempt to throw off the interviewee to illicit more honest answers.

Determining Interviewee Consistency: To enhance the viability of the disclosed systems it may be beneficial to confirm, substantially or at several discrete points during an interview, that the interviewee is a single specific individual and that the person acting as the interviewee has not changed during the interview. Such confirmation may detect for example and without limitation, whether a person who has responded to one or more interview questions has been replaced with a different individual at some point during the interview.

Various approaches are envisioned for ensuring interviewee identify consistency. According to certain approaches the apparatus and methods used to ensure interviewee identity consistency may be all located or implemented near the location where the relevant local appliance 200 is located. According to other approaches, the detection apparatuses may be located near the local appliance, but the processing may be done at the central server. In still other approaches, the apparatuses and processes are distributed, with some being located near the local appliance 200 and others apart.

One approach for ensuring identity interview consistence may be to use the camera to periodically or continuously assess the body physique of the interviewee and provide an alarm indication if the detected body physique of the interview changes in an unexpected manner or moves out of the frame.

In embodiments where a force platform is used, as an alternative to, or in addition to the processes described herein, interviewee consistency may be assessed by monitoring the output of the force platform to observe movements that are either unexpected or consistence with a change in the interviewee and/or for an unexpected change of weight during the interview. Upon the detection of such an unexpected event, an alarm or indication reflecting a potential interviewee identity change may be raised.

In addition to confirming the consistent identity of the interviewee, the distributed discernment system may further implement processes to determine that the interviewee is not inappropriately influenced by others during the interview. For example, the distributed discernment system—either through a local process run at the human interface system 120 or through a process run at the discernment server system 110—may seek to detect: (a) non-interviewee speech of the type that would suggest that a third-party is providing answers to the interviewee; (b) third-party appearance in the frame of the camera; (c) unexpected changes in the detected weight on a force platform (suggesting third-party appearance) or any other indicia of interference.

DISTRIBUTED PROCESSING: One important benefit that may be provided by a distributed processing system constructed in accordance with certain teachings of this disclosure may be that the processing operations necessary to implement the system may be distributed across the various devices comprising the system For example, the initial calibration steps, the initial "interview start" detection, and the interviewee consistency processes may all be implemented at a local level through processes operating on the various human interface system 120s. One benefit of this embodiment may be that it can reduce the extent of information that needs to be transferred from the local appliance 200 to the central server, thus freeing up bandwidth that may be used for the communication of other information or reducing the overall bandwidth requirements. For example, in such embodiments, the local appliance 200 may need only to communicate an alert signal to the central server if its local processing detects a change (or potential change) in the interviewee identity, In one preferred embodiment, the questions may be presented to the interviewee through the use of a three-dimensional video representation of a human agent. There are various ways in which the video feed associated with the human agent may be generated and presented to the interviewee.

In accordance with one embodiment, the video data for each question (including the video data necessary to present the animated human agent to the interviewee) may be generated in any suitable manner and stored and maintained in a memory system accessible to discernment server system. In such embodiments, each time a question or instruction is to be presented to an interviewee, the distributed server system will stream the video feed (and potentially the accompanying audio feed) to the appropriate human interface system 120 associated with that interview.

The described embodiment may require the maintenance of a large number of pre-recorded video segments and, in instances where there are a large number of local appliances involved in a large number of individual interviews, the need for the discernment server system 110 to access and transmit a large number of video segments to the local appliances. This may give rise to storage and bandwidth issues.

Accordingly, alternate embodiments are envisioned where the video (and potentially audio) segments associated with an instruction or question to be presented to an interviewee are rendered in substantially real time by the distributed server system. This embodiment, therefore, reduces the need for the remote storage of various pre-rendered video clips. This embodiment, however, still may have a need for transmission of the rendered video segments to each of the individual human interface system 120s and, therefore, a need for substantial bandwidth.

Yet a further embodiment is envisioned wherein all of the video rendering is done within the human interface system 120s, e.g., within local appliances. In this embodiment, the discernment server system 110 provides each of the human interface system 120s (e.g., each local appliance) with the data required to render a video (and potentially an audio/visual) presentation of all or various parts of the interview.

For example, in such an embodiment, each human interface system 120 could be programmed—at initial provisioning—with a robust 3D model of a virtual human interviewer. Such a model may take the form, for example, of a human model created using a program such as UNREAL ENGINE's MetaHuman Creator program. After such provisioning, the discernment server system 110 need only then provide the data files necessary to "animate" the virtual human interviewer to conduct the desired interview. The local human interface system 120s would then render the received data to generate the image and other associated stimuli provided to the interviewee during the interview.

One advantage of the local rendering approach described herein is that it may significantly reduce the overall bandwidth necessary for the communication channels. In such embodiments, the communication channels need not support significant data transfers between the local human interface system 120s and the discernment server system(s) which may therefore enable a given system to support a large number of individual human interface system 120s (making the overall system very scalable) and/or enable the proper sizing of a system for a given desired workload to reduce cost and promote efficiency. In other words, in certain systems the processing required by the system may be distributed between the local devices and the discernment server system 110 so that the overall costs of the system may be minimized.

A further advantage of the distributed approach described above is that it may permit readily tailoring of the system to specific applications. For example, in an application where the described system will be used in an international airport—and where individuals of various cultural backgrounds and native languages will be traveling—different human interface system 120s may be provisioned to provide differently appearing virtual agents for interacting with passengers form different locations. Such different virtual agents could be tailored—in appearance, voice pitch/tone, etc.—to passengers traveling to/from specific countries or regions since, in such an embodiment, the rendering of the virtual agent data file would all be done locally, the discernment server system 110 may not have to bear the burden of rendering multiple different appearing agents and the communication may not have to bear the data traffic associated with such actions.

A further advantage of the distributed approach described above, may be that it allows various authorized users to interact with the distributed discernment system in various ways. For example, in applications where such a system is used for employment pre-screening and post-employment evaluation, the distributed discernment system could allow authorized administrators to review various interview data and reports suitable for their roles. For example, a given manager may be able to review select post-employment interview data only for employees under their supervision, while a company-wide security officer may have access to all employee interview data.

A combination of very thin clients with a distributed system may be advantageous in some situations. For example, an entry gate at a sporting event may have multiple queues for people to enter. In this exemplary embodiment, one distributed discernment system may be placed at the gate for one queue, and several other thin client discernment systems may service the other queues. Each of the thin client discernment systems would be linked via a high-speed network to the nearby distributed discernment system so they could each draw on the resources of the distributed discernment system. The resources that the distributed discernment system may offer to the thin client systems may include but would not be limited to: a link to a cloud-based processing system; a codec for coding/decoding video streams; encryption services; memory and processing services.

As a nonlimiting example, the distributed discernment system may be loaded with several virtual interview agents, such as virtual men and women. When an interviewee is identified by a thin client, a virtual interview agent would be retrieved by the thin client and the interview would commence. At the end of each interview, each thin client may then be empowered to either reuse the virtual interview agent, or discard it and retrieve another. In this way, the greater resources of the distributed discernment system may be utilized by a plethora of less costly thin clients without any disadvantages of inferior service.

The system described herein can be used in a variety of different applications.

For example, the disclosed system can be used to assess insider threats to an organization. In general, an insider threat is a malicious threat that comes from people within an organization such as employees, vendors, contractors, etc. Insider threats are often difficult to identify because the individuals posing the insider threats often have personal, professional, and friendship relationships with those operating to detect the threats.

Various processes can be employed for assessing insider threats using embodiments of the described distributed discernment system. In accordance with one embodiment, all employees (and potentially vendors, contractors, etc.) of an organization may be subjected to interviews using the system on both a regular and on a random basis. The interview stimuli provided during such interviews could include questions designed to identify threats. For example, questions such as "Have you misused company data?" could be presented. As another example, images of equipment or files that have gone missing from the company could be visually displayed to determine the response of the individuals to the display. Data suggesting an insider threat could be presented to the appropriate management and security staff of the entity utilizing the system.

A benefit of the above-described approach is that the interviews could be conducted at a single location using a desktop human interface system 120 under conditions that are not likely to suggest to an individual interviewee that they are under suspicion. Since all employees would be required to undergo the described interview process, the conduction of an interview would not necessarily give rise to special alarm. The ability to conduct such broad interviews of employees on a regular basis on a cost and time-effective basis is a benefit of the described system that is not necessarily enabled by individual kiosk systems, where cost and time limitations may preclude the number and type of interviews required by this system.

The systems and processes disclosed and taught herein may also be used to identify non-malicious but unauthorized behavior. For example, a company policy may forbid employees from using their work computers for personal use. While not overtly malicious, employees using their work computers for social media may be placing the company at risk by opening a path for bad actors outside of the company to access company confidential information. Processes and systems described and taught herein may be applied to identifying such unauthorized behavior.

Another application of the present system concerns access control where a distributed system constructed in accordance with certain teachings of the present disclosure could be used to both verify that a given individual is allowed to have access to a particular event (e.g., a sporting event) and assess the potential that such an individual may engage in inappropriate conduct at the event. For such applications, a multi-layered embodiment of the described system—using several different human interface system 120s—may be beneficial.

For example, within the context of access to a passenger flight, a multilayered system using smartphone based human interface system 120s, small-scale kiosk human interface system 120s, local appliance 200 systems, and dedicated stationary systems could be used.

Figure 5:
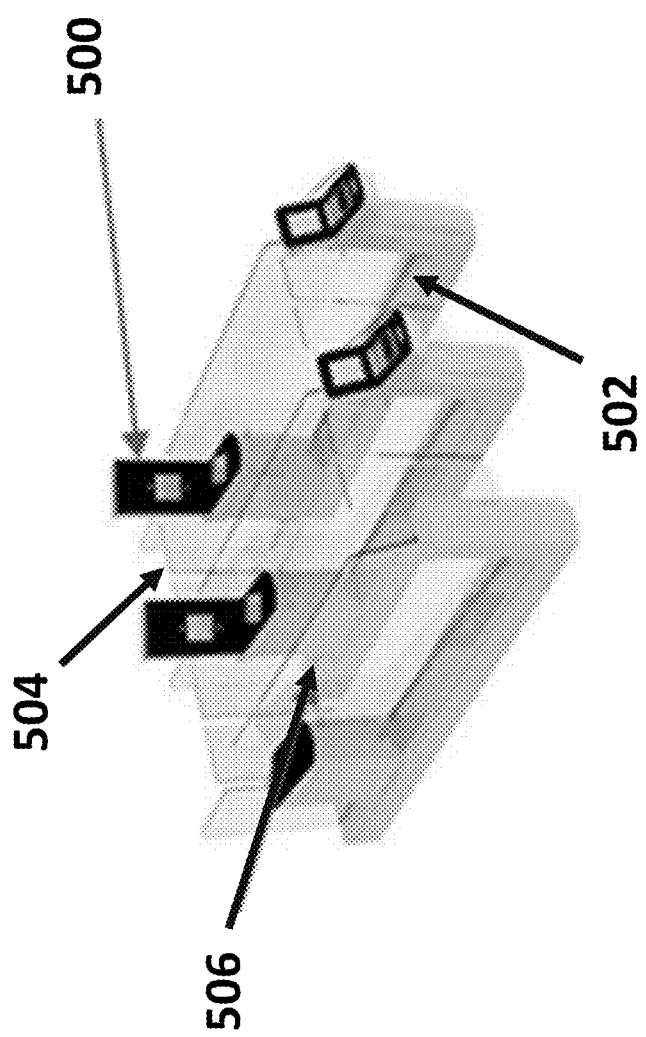
FIG. 5 illustrates a human interface system 120 with minimal input/output apparatus for use as a secondary screening station in an airport.

In such an embodiment a person desiring to access a passenger flight could initially access the system through a smartphone base human interface system 120. The smartphone system could then follow an interview process described above to verify the identity of the individual participating in the interview and assess the potential that the individual will engage in malicious or unauthorized conduct in connection with the desired flight. If this initial interview screening indicated that the particular interviewee posed a very low risk on malicious or unauthorized behavior, then the individual may be subject only to minimal secondary screening. For example, such a low-risk individual—e.g., a frequent traveler, with no suspect history, whose responses to the interview stimuli showed no anomalies—could be allowed to pass through the boarding gate with, perhaps, an abbreviated interview conducted by a human interface system 120 with minimal detecting capabilities, such as a tablet, with only visual and audio outputs inputs that is coupled to a gate. One exemplary human interface system 120 is shown in FIG. 5. FIG. 5 illustrates a human interface system 120 with minimal input/output apparatus for use as a secondary screening station in an airport.

Passengers unable to be classified as very low risk as a result of the smartphone-type interview (or passengers who do not participate in such an interview) would then be subject to a more intense secondary screening at the airport. For example, most passengers could be subjected to a screening interview using a tablet-like human interface system 120 in the form of a local appliance, while others could be randomly (or based on select criteria) subject to a more rigorous interview using a desktop human interface. Still further, passengers identified as having above a threshold likelihood for malicious or unauthorized conduct (or who exhibited signs of deception) could be subject to more throughout interviews, using more advanced and sophisticated human interface systems 120.

As reflected in FIG. 5, in the illustrated example various passenger screening lanes are established through the use acoustic isolation structures 506 which separate one lane from another. Each of the plurality of passenger screening lanes includes an entry gate 502 and an exit gate 504 which together define an interior screening space. Entry to the screening space is controlled through an access control device 502 which may take the form of a conventional airport access device that scans for a valid boarding pass and opens the entry gate 502 upon the detection of a valid boarding pass. The operation of the exit gate 504 may be controlled by a screening pseudo-kiosk 500 that includes, as one element, a local human interface device of the type discussed above in connection with device 120 of FIG. 1. The human interface device within the kiosk may perform a screening interview and either open exit gate 504 (if no, or a low level, risk of deception is detected) or notify security that additional screening is required if more than a certain level of likely deception is detected.

Note that the distributed discernment system described herein could be used in conjunction with a human interview. Thus, any heightened airport security screening could involve a human interviewer providing questions, with a human interface system 120 operating simultaneously to collect data associated with the interview and to pass such data to the human interviewer (or others) for use in carrying out or assessing the content of the interview.

Another process in which a distributed discernment system of the type disclosed herein could be used is in connection with medical or mental health evaluation and/or treatment. For example, for individuals who may be subject to state changes resulting from a change in their state (e.g., as a result of a manic incident, a stroke, significant anxiety, failure to take medications, etc.) a home-based human interface system 120 could be used that could report to a licensed professional or an authorized family member both: (a) that the individual using the device has completed a regularly-scheduled interview and (b) whether the results of that interview suggest that the individual is in a state requiring follow-up action or attention. For example, children and others subject to manic states are often prescribed medication to take on a daily basis. Subjecting such interviewees to daily interviews using a home-based human interface system 120 could allow regular and automatic assessment of whether each individual is compliant with their medications and/or whether the medications are operating properly. If the interview suggests that the individual has not taken their medication—or that the interviewee is experiencing a manic state—a notice that further action is warranted could be provided.

Note that the above-described example is one where the use of a virtual interviewer could permit the system to be uniquely tailored for use with children. For example, while a child may be hesitant to interact with a stern-appearing virtual interviewer, a virtual interviewer uniquely tailored to that child, such as a cartoonish character in the form of their favorite animal, may result in a situation where the child is both comfortable and eager to participate in an interview as described above.

Note that the described system may also enable the distributed discernment system of the present invention to be used in a therapeutic manner. For example, if an interview indicates that the interviewee is experiencing sever anxiety, the system could—in addition to alerting the appropriate professional—be designed to respond empathetically (e.g., "You seem upset. Is there something that you want to share?" or "You appear angry. Have you remembered to take your medication this morning?").

Other and further embodiments utilizing one or more aspects of the inventions described above can be devised without departing from the spirit of Applicant's invention. Further, the various methods and embodiments of the methods of manufacture and assembly of the system, as well as location specifications, can be included in combination with each other to produce variations of the disclosed methods and embodiments. Discussion of singular elements can include plural elements and vice-versa.

The order of steps can occur in a variety of sequences unless otherwise specifically limited. The various steps described herein can be combined with other steps, interlineated with the stated steps, and/or split into multiple steps. Similarly, elements have been described functionally and can be embodied as separate components or can be combined into components having multiple functions.

The inventions have been described in the context of preferred and other embodiments and not every embodiment of the invention has been described. Obvious modifications and alterations to the described embodiments are available to those of ordinary skill in the art. The disclosed and undisclosed embodiments are not intended to limit or restrict the scope or applicability of the invention conceived of by the Applicants, but rather, in conformity with the patent laws, Applicants intend to protect fully all such modifications and improvements that come within the scope or range of equivalent of the following claims.

What is claimed is:

1. A distributed discernment system comprising:
   a discernment server including a processer running a diagnostic program and server interface permitting bi-directional communications to and from the discernment server; and
   a plurality of human interface devices, each human interface device including a display capable of presenting a video segment of a virtual human interviewer asking a question to an interviewee interacting with the human interface device, a plurality of sensors capable of detecting various responses of a human interviewee to each presented question, and a system interface permitting bi-directional communications to and from the human interface system, wherein:
   the diagnostic program running on the discernment server is adapted to generate interview instructions to be provided to a plurality of human interface devices over the communications network, wherein the instructions provided to a given human interface device are intended to cause the human interface device to present certain stimuli to a human interviewee interacting with the given human interface device;
   each of the plurality of human interface devices is adapted receive interview instructions from the discernment server over the communication network and, in response to such instructions,
   present a video segment of a virtual human interviewer asking a question to a human interviewee, where at least the content of the question is determined from the interview instructions;
   receive sensor data reflecting the human interviewee's reaction to the question;
   communicate at least some of the received sensor data to the discernment server using the communication network; and
   the discernment server is adapted to receive data from each of a plurality of the human interface devices and analyze such data to provide an assessment of the state of the human interviewee interacting with the human interface device.

2. The discernment detection of claim 1 wherein the video segment resulting in the image of the virtual human being is rendered locally at each of the plurality of human interface devices from information provided by the discernment server.

3. The distributed discernment system of claim 1 wherein the discernment server system includes storage for storing reports related to at least one interview conducted by one of the human interface devices.

4. The distributed discernment system of claim 3 further comprising a plurality of client interface devices and a plurality of client communication links between such client interface devices and the discernment server system wherein each client interface device is configured to permit authorized users to access reports stored in the discernment system relating to at least on completed interview.

5. The distributed discernment system of claim 1 wherein each of the plurality of human interface devices includes both a face camera for generating sensor signals reflective of the interviewee's face during an interview and an eye tracking camera for generating sensor signals reflective of the position and movement of an interviewee's eyes during an interview.

6. The distributed discernment system of claim 1 wherein each of the plurality of human interface devices takes the form of a tablet device including a touch-screen display, a face camera, an eye tracker, a microphone, and a speaker.

7. A distributed system for simultaneously conducting a plurality of interviews with a plurality of human interviewees, where data associated with each interview is processed to generate an indication of likely deception by the interviewee, the distributed system comprising:
   (a) a plurality of mobile integrated appliances, each mobile interface appliance including: (i) a touch-screen display, (ii) a system on a module ("SOM") element, the SOM element providing computing, memory, storage, and wireless connectivity functionalities; (iii) a plurality of sensors that permit the local appliance to detect various attributes and characteristics of an interviewee undergoing an interview and wherein each mobile interface appliance includes a upper bezel positioned above the top of the touch-screen display and a lower bezel positioned below the bottom of the touch-screen display and wherein the sensors include a face camera positioned within the upper bezel, at least a first microphone positioned within the upper bezel, an eye tracker positioned within the lower bezel, and a speaker positioned within the lower bezel; and (iv) a communication interface adapted to receive stimuli data associated with stimuli to be presented by the mobile integrated appliance to an interview and to transmit sensor data reflective of the output of the sensors during a period where stimuli is presented to an interviewee; and
   (b) a discernment server capable of communicating with each of the plurality of mobile integrated appliances, the discernment server comprising: a processing system running one or more application programming interfaces for enabling communication between the discernment server and each of the plurality of mobile integrated devices and at least one discernment algorithm for processing sensor data received from at least one of the plurality of mobile integrated devices to: (i) receive sensor data transmitted by the at least one of the plurality of mobile integrated devices; (ii) in response to the received sensor data, generate stimuli data to be provided to the at least one of the plurality of mobile integrated devices, and (iii) in response to the received sensor data, generate report data reflecting an association between the received sensor data and deception.

8. The distributed system of claim 7 where each mobile integrated appliance further includes at least one side bezel located to one side of the display and a second microphone positioned within the side bezel.

9. The distributed system of claim 7 wherein each of the plurality of mobile integrated devices includes a processor capable of rendering audio and video images for display on the touchscreen display in response to stimuli data received from the discernment server.

10. The distributed system of claim 7 wherein each of the plurality of mobile integrated devices is configured to identify the identity of a human interviewee interacting with the mobile interface device and generate a notification that can be provided to the discernment server if the identity of the human interacting with the mobile interface device changes.

11. The distributed system of claim 7 wherein the communication interface is a wired interface.

12. The distributed system of claim 7 wherein the discernment server utilizes at least one machine learning model to generate the report data.

13. A distributed detection system for simultaneously conducting a plurality of interviews with a plurality of human interviewees, comprising:
   (a) a plurality of human interface devices, each human interface device including: a processor for receiving sensor signals from each of a plurality of sensors, wherein the received signals reflect one or more conditions of a human interview interacting with the human interface device; a communications interface for receiving and transmitting communication signals to and from a remote server; and a display interface for providing audio and video display signals to a display device; and
   (b) a discernment server capable of communicating with each of the plurality of human interface devices, the discernment server comprising an input interface configured to receive communication signals from each of the plurality of human interface devices, wherein the received communication signals reflect at lease some of the sensor signals received by the human interface device; a processor communicating with the interface and adapted to process the received communication signals to assess the state of the human interviewee associated with the received communication signals; and an output interface adapted to transmit output signals to at least one of the human interface devices, the output signals corresponding to stimuli to be presented to a human interview.

14. The discernment system of claim 13 wherein at least one of the human interface devices comprises a home discernment device defining a first port capable of receiving input signals from a microphone; a second port capable of receiving input signals from a video camera; a third port capable of providing output video signals to a display device; and a wireless communication interface.

15. The discernment system of claim 14 wherein the home discernment device includes a fourth port capable of receiving input signals from an eye tracking device.

16. The discernment system of claim 13 where at least one of the human interface devices takes the form of a tablet that includes a touch-screen display and a speaker in communication with the display interface; a microphone and an eye-tracker in communication with the input interface and wherein the output interface supports wireless communications.

17. The discernment system of claim 16 wherein the at least one of the human interface devices further includes a face camera for providing signals reflective of the movements of the face of a human interviewee over a period of time.

18. The discernment system of claim 16 wherein the at least one of the human interface devices includes a battery, such that the device can be operated without an external power connection.

19. The discernment system of claim 16 wherein at least one of the human interface devices is included within a screening kiosk and wherein the screening kiosk is coupled to a gate, and wherein the screening kiosk is adapted to open the gate based at least in part on sensor signals received by the at least one human interface device.

20. The discernment system of claim 17 further including at least two acoustic isolation structures, wherein the screening kiosk is positioned within a screening lane defined by the at least to acoustic isolation structures.

* * * * *